(12) United States Patent
Chintala et al.

(10) Patent No.: US 10,772,947 B2
(45) Date of Patent: Sep. 15, 2020

(54) HPV VACCINE FORMULATIONS COMPRISING ALUMINUM ADJUVANT AND METHODS OF PRODUCING SAME

(71) Applicant: Merck Sharp & Dohme Corp., Rahway, NJ (US)

(72) Inventors: Ramesh V. Chintala, Chalfont, PA (US); Akhilesh Bhambhani, Doylestown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/378,696

(22) Filed: Dec. 14, 2016

(65) Prior Publication Data

US 2017/0157238 A1 Jun. 8, 2017

Related U.S. Application Data

(63) Continuation of application No. 14/126,992, filed as application No. PCT/US2012/043694 on Jun. 22, 2012, now abandoned.

(60) Provisional application No. 61/500,829, filed on Jun. 24, 2011.

(51) Int. Cl.

| | |
|---|---|
| A61K 39/12 | (2006.01) |
| A61K 39/39 | (2006.01) |
| A61K 47/02 | (2006.01) |
| A61K 47/18 | (2017.01) |
| A61K 47/26 | (2006.01) |
| A61K 9/19 | (2006.01) |
| A61K 9/00 | (2006.01) |
| C12N 7/00 | (2006.01) |
| A61K 39/00 | (2006.01) |

(52) U.S. Cl.
CPC ............ *A61K 39/12* (2013.01); *A61K 9/0019* (2013.01); *A61K 9/19* (2013.01); *A61K 39/39* (2013.01); *A61K 47/02* (2013.01); *A61K 47/183* (2013.01); *A61K 47/26* (2013.01); *C12N 7/00* (2013.01); *A61K 2039/5258* (2013.01); *A61K 2039/55505* (2013.01); *A61K 2039/70* (2013.01); *C12N 2710/20023* (2013.01); *C12N 2710/20034* (2013.01)

(58) Field of Classification Search
None
See application file for complete search history.

(56) References Cited

U.S. PATENT DOCUMENTS

| | | | |
|---|---|---|---|
| 5,888,516 A | 3/1999 | Jansen et al. | |
| 5,902,565 A | 5/1999 | Cox et al. | |
| 6,251,678 B1 * | 6/2001 | Volkin | A61K 39/12 424/204.1 |
| 2004/0213798 A1 | 10/2004 | Maa et al. | |
| 2006/0067943 A1 | 3/2006 | Maa et al. | |
| 2008/0226729 A1 | 9/2008 | Sullivan et al. | |

FOREIGN PATENT DOCUMENTS

| | | |
|---|---|---|
| CA | 2443214 | 3/2001 |
| CA | 2746690 | 6/2010 |
| EP | 0130619 | 3/1989 |
| JP | 2010502747 | 1/2010 |
| JP | 2010520874 | 6/2010 |
| WO | 1998013065 | 4/1998 |
| WO | 2000045841 | 8/2000 |
| WO | 2008079464 | 7/2008 |
| WO | 2008112125 | 9/2008 |
| WO | 2008115641 | 9/2008 |
| WO | 2008118691 | 10/2008 |
| WO | 2009108689 | 9/2009 |
| WO | WO2009108689 A1 * | 9/2009 |
| WO | 2011017070 | 2/2011 |

OTHER PUBLICATIONS

Johnson et al. J. Pharm. Sci. 2002, 91: 914-922.*
Moscicki. J. Adolescent Health. 2008. 43: S26-S40.*
A. Bhambhani et al., Lyophilization Strategies for Development of a High-Concentration Monoclonal Antibody Formulation: Benefits and Pitfalls, American Pharmaceutical Review, 2010, 31-38, 13(1).
A. L. Clausi et al., Inhibition of Aggregation of Aluminum Hydroxide Adjuvant during Freezing and Drying, Journal of Pharmaceutical Sciences, 2008, 2049-61, 97.
Baylor, N. W., Aluminum salts in vaccines—US perspective, Vaccine, 2002, S18-S23, 20.
B.S. Chang et al, Surface-Induced Denaturation of Proteins during Freezing and Its Inhibition by Surfactants, Journal of Pharmaceutical Sciences, 1996, 1325-30, 85(12).
J.C. Cook et al., Purification of Virus-like Particles of Recombinant Human Papillomavirus Type 11 Major Capsid Protein L1 from *Saccharomyces cerevisiae*, Protein Expression and Purification, 1999, 477-84, 17.
D. M. Matthias, et al., Freezing temperatures in the vaccine cold chain: A systematic literature review, Vaccine, 2007, 3980-86, 25(20).
Erik B Lindblad, Aluminium compounds for use in vaccines, Immunology and Cell Biology, 2004, 497-505, 82.

(Continued)

*Primary Examiner* — Nianxiang Zou
(74) *Attorney, Agent, or Firm* — Nichole M. Valeyko; Laura M. Ginkel

(57) ABSTRACT

The invention provides human papillomavirus (HPV) antigen formulations which show increased antigen stability. More specifically, the invention provides stable HPV formulations comprising HPV virus-like particles (VLPs) bound to an aluminum salt adjuvant and further comprise a combination of sucrose and mannitol. The vaccine formulations of the invention are stable following freeze-thaw and freeze-drying. Also provided are lyophilized and frozen HPV vaccine formulations comprising HPV VLPs of at least one HPV type adsorbed onto an aluminum salt adjuvant, sucrose, and mannitol. Methods of making the stable vaccine formulations of the invention are also provided.

11 Claims, 19 Drawing Sheets

(56) References Cited

OTHER PUBLICATIONS

J. Klein et al., Analysis of Aluminum Hydroxyphosphate Vaccine Adjuvants by 27Al MAS NMR, Journal of Pharmaceutical Sciences, 2000, 311-21, 89(3).
Johnson et al., Mannitol-Sucrose Mixtures—Versatile Formulations for Protein Lyophilization, J. Pharm. Sci., 2002, 914-922, 91.
Kazzaz et al., Encapsulation of the immune potentiators MPL and RC529 in PLG microparticles enhances their potency, Journal of Controlled Release, Elsevier, 2006, 566-573, 110(3).
L. Wolff et al., Protection of aluminum hydroxide during lyophilisation as an adjuvant for freeze-dried vaccines, Colloids and Surfaces A: Physicochem. Eng. Aspects, 2008, 116-126, 330.
L.J. Braun et al., Characterization of a thermostable hepatitis B vaccine formulation, Vaccine, 2009, 4609-4614, 27.
L.J. Braun et al., Development of a freeze-stable formulation for vaccines containing aluminum salt adjuvants, Vaccine, 2009, 72-79, 27.
Le Tallec et al., Cervarix, the GSK HPV-16/HPV-18 AS04-adjuvanted cervical cancer vaccine, demonstrates stability upon long-term storage and under simulated cold chain break conditions, Human Vaccines, 2009, 467-474, 5(7).
M.J. Caulfield et al., Effect of Alternative Aluminum Adjuvants on the Absorption and Immunogenicity of HPV16 L1 VLPs in Mice, Human Vaccines, 2007, 139-146, 3.
Moscicki et al., HPV Vaccines: Today and in the Future, Journal of Adolescent Health 43, 2008, S26-S40, 43.
R. S. Lowe et al., Human Papillomavirus Type 11 (HPV-11) Neutralizing Antibodies in the Serum and Genital Mucosal Secretions of African Green Monkeys Immunized with HPV-11 Virus-like Particles Expressed in Yeast, Journal of Infectious Diseases, 1997, 1141-45, 176.
T. Clapp, et al., Vaccines with Aluminum-containing Adjuvants: Optimizing Vaccine Efficacy and Thermal Stability, Journal of Pharmaceutical Sciences, 2011, 388-401, 100(2).
Y-F. Maa et al., Stabilization of Alum-Adjuvanted Vaccine Dry Powder Formulations: Mechanism and Application, Journal of Pharmaceutical Sciences, 2003, 319-332, 92(2).
Zhao et al., Characterization of virus-like particles in GARDASIL by cryo transmission electron microscopy, Human Vaccines & Immunotherapeutics, 2014, 734-739, 10:3.

\* cited by examiner

| Buffer | Buffer Code | NaCl (mM) | Mannitol w/v (%) | Glycine w/v (%) | Sucrose w/v (%) |
|---|---|---|---|---|---|
| Buffer-A | B-1 | 0 | 5 | – | – |
| | B-7 | 150 | 5 | – | – |
| | B-13 | 320 | 5 | – | – |
| Buffer-B | B-2 | 0 | – | – | – |
| | B-8 | 150 | – | – | – |
| | B-14 | 320 | – | – | – |
| Buffer-C | B-3 | 0 | 5 | – | 2 |
| | B-9 | 150 | 5 | – | 2 |
| | B-15 | 320 | 5 | – | 2 |
| Buffer-D | B-4 | 0 | 6 | – | 4 |
| | B-10 | 150 | 6 | – | 4 |
| | B-16 | 320 | 6 | – | 4 |
| Buffer-E | B-5 | 0 | – | – | 8 |
| | B-11 | 150 | – | – | 8 |
| | B-17 | 320 | – | – | 8 |
| Buffer-F | B-6 | 0 | – | 2 | 1 |
| | B-12 | 150 | – | 2 | 1 |
| | B-18 | 320 | – | 2 | 1 |

FIG.1

| Buffer | Buffer Code | NaCl (mM) | Cake Appearance | | | |
|---|---|---|---|---|---|---|
| | | | T=0 | | T=1M at 45°C | |
| | | | Pre-cooled | Flash freeze | Pre-cooled | Flash freeze |
| Buffer-A | B-1 | 0 | ++++ | ++++ | ++++ | ++++ |
| | B-7 | 150 | +++ | +++ | +++ | +++ |
| | B-13 | 320 | ++++ | ++++ | ++++ | ++++ |
| Buffer-B | B-2 | 0 | ++/+++ | + | ++/+++ | + |
| | B-8 | 150 | +++ | +/++ | +++ | +/++ |
| | B-14 | 320 | ++ | ++ | ++ | ++ |
| Buffer-C | B-3 | 0 | ++++ | ++++ | ++++ | ++++ |
| | B-9 | 150 | ++/+++ | ++ | ++/+++ | ++ |
| | B-15 | 320 | ++ | ++ | ++ | ++ |
| Buffer-D | B-4 | 0 | ++++ | ++++ | ++++ | ++++ |
| | B-10 | 150 | ++/+++ | ++/+++ | ++/+++ | ++/+++ |
| | B-16 | 320 | ++ | ++ | ++ | ++ |
| Buffer-E | B-5 | 0 | + | + | +* | +* |
| | B-11 | 150 | + | + | +* | +* |
| | B-17 | 320 | + | + | +* | +* |
| Buffer-F | B-6 | 0 | +++/++++ | +++ | +++/++++ | +++ |
| | B-12 | 150 | + | + | + | + |
| | B-18 | 320 | + | + | + | + |

*Cake color change to yellow/brown

FIG.7

| Buffer | Buffer Code | NaCl (mM) | Reconstitution Time (sec) | | | |
| --- | --- | --- | --- | --- | --- | --- |
| | | | T=0 | | T=1M at 45°C | |
| | | | Pre-cooled | Flash freeze | Pre-cooled | Flash freeze |
| Buffer-A | B-1 | 0 | 12/13 | 15/11 | 5 | 8 |
| | B-7 | 150 | 15/10 | 8/12 | 8 | 6 |
| | B-13 | 320 | 12/5 | 10/13 | 10 | 5 |
| Buffer-B | B-2 | 0 | 5/8 | 5/5 | 10 | 6 |
| | B-8 | 150 | 5/10 | 4/8 | 7 | 5 |
| | B-14 | 320 | 15/12 | 8/12 | 10 | 7 |
| Buffer-C | B-3 | 0 | 11/14 | 10/11 | 9 | 8 |
| | B-9 | 150 | 10/12 | 8/10 | 6 | 6 |
| | B-15 | 320 | 20/15 | 20/15 | 10 | 8 |
| Buffer-D | B-4 | 0 | 9/10 | 9/11 | 10 | 6 |
| | B-10 | 150 | 5/8 | 5/8 | 6 | 8 |
| | B-16 | 320 | 12/10 | 10/7 | 8 | 10 |
| Buffer-E | B-5 | 0 | 107/135 | 162/187 | 130 | 112 |
| | B-11 | 150 | 120/150 | 120/150 | 45 | 140 |
| | B-17 | 320 | 90/120 | 120/160 | 130 | 180 |
| Buffer-F | B-6 | 0 | 8/5 | 4/8 | 7 | 10 |
| | B-12 | 150 | 5/10 | 8/12 | 30 | 20 |
| | B-18 | 320 | 15/8 | 7/15 | 13 | 8 |

FIG.8

| Buffer | Buffer Code | NaCl (mM) | Shake Test Time (min) | |
|---|---|---|---|---|
| | | | Pre-cooled | Flash freeze |
| Buffer-A | B-1 | 0 | 10 | 10 |
| | B-7 | 150 | 11 | 11 |
| | B-13 | 320 | 12 | 12 |
| Buffer-B | B-2 | 0 | 10 | 10 |
| | B-8 | 150 | 6 | 6 |
| | B-14 | 320 | 5 | 5 |
| Buffer-C | B-3 | 0 | 12 | 12 |
| | B-9 | 150 | 12 | 12 |
| | B-15 | 320 | 11 | 11 |
| Buffer-D | B-4 | 0 | >15 | >15 |
| | B-10 | 150 | 15 | 15 |
| | B-16 | 320 | >15 | >15 |
| Buffer-E | B-5 | 0 | >15 | >15 |
| | B-11 | 150 | >15 | >15 |
| | B-17 | 320 | >15 | >15 |
| Buffer-F | B-6 | 0 | 10 | 10 |
| | B-12 | 150 | >15 | >15 |
| | B-18 | 320 | >15 | >15 |

FIG.9

| Buffer | Buffer Code | Cake Appearance at 2-8 °C | | | |
|---|---|---|---|---|---|
| | | T=0 | T=1M | T=3M | T=6M |
| Buffer-B | Buffer 14 | + | + | + | + |
| Buffer-C | Buffer 3 | ++++ | ++++ | ++++ | ++++ |
| | Buffer 15 | ++/+++ | ++/+++ | ++/+++ | ++/+++ |
| Buffer-D | Buffer 4 | ++++ | ++++ | ++++ | ++++ |
| | Buffer 16 | ++ | ++ | ++ | ++ |

FIG.13A

| Buffer | Buffer Code | Cake Appearance at 25 °C | | |
|---|---|---|---|---|
| | | T=1M | T=3M | T=6M |
| Buffer-B | Buffer 14 | + | + | + |
| Buffer-C | Buffer 3 | ++++ | ++++ | ++++ |
| | Buffer 15 | ++/+++ | ++/+++ | ++/+++ |
| Buffer-D | Buffer 4 | ++++ | ++++ | ++++ |
| | Buffer 16 | ++ | ++ | ++ |

FIG.13B

| Buffer | Buffer Code | Cake Appearance at 37 °C | |
|---|---|---|---|
| | | T=1M | T=3M |
| Buffer-B | Buffer 14 | + | + |
| Buffer-C | Buffer 3 | ++++ | ++++ |
| | Buffer 15 | ++/+++ | ++/+++ |
| Buffer-D | Buffer 4 | ++++ | ++++ |
| | Buffer 16 | ++ | ++ |

FIG.13C

| Buffer | Buffer Code | Cake Appearance at -70 °C |
|---|---|---|
| | | T=6M |
| Buffer-B | Buffer 14 | + |
| Buffer-C | Buffer 3 | ++++ |
| | Buffer 15 | ++/+++ |
| Buffer-D | Buffer 4 | ++++ |
| | Buffer 16 | ++ |

FIG.13D

| Buffer | Buffer Code | Cake Appearance at 2-8 °C ||||
|---|---|---|---|---|---|
| | | T=0 | T=1M | T=3M | T=6M |
| Buffer-B | Buffer 14 | + | + | + | + |
| Buffer-C | Buffer 3 | ++++ | ++++ | ++++ | ++++ |
| | Buffer 15 | ++/+++ | ++/+++ | ++/+++ | ++/+++ |
| Buffer-D | Buffer 4 | ++++ | ++++ | ++++ | ++++ |
| | Buffer 16 | ++ | ++ | ++ | ++ |

FIG.14A

| Buffer | Buffer Code | Cake Appearance at 25 °C |||
|---|---|---|---|---|
| | | T=1M | T=3M | T=6M |
| Buffer-B | Buffer 14 | + | + | + |
| Buffer-C | Buffer 3 | ++++ | ++++ | ++++ |
| | Buffer 15 | ++/+++ | ++/+++ | ++/+++ |
| Buffer-D | Buffer 4 | ++++ | ++++ | ++++ |
| | Buffer 16 | ++ | ++ | ++ |

FIG.14B

| Buffer | Buffer Code | Cake Appearance at 37 °C ||
|---|---|---|---|
| | | T=1M | T=3M |
| Buffer-B | Buffer 14 | + | + |
| Buffer-C | Buffer 3 | ++++ | ++++ |
| | Buffer 15 | ++/+++ | ++/+++ |
| Buffer-D | Buffer 4 | ++++ | ++++ |
| | Buffer 16 | ++ | ++ |

FIG.14C

| Buffer | Buffer Code | Cake Appearance at −70 °C |
|---|---|---|
| | | T=6M |
| Buffer-B | Buffer 14 | + |
| Buffer-C | Buffer 3 | ++++ |
| | Buffer 15 | ++/+++ |
| Buffer-D | Buffer 4 | ++++ |
| | Buffer 16 | ++ |

FIG.14D

| Buffer Code | Shake Test Time (min) at 2–8 °C | | | | | | | |
|---|---|---|---|---|---|---|---|---|
| | F/T | | | | LYO | | | |
| | T=0 | T=1M | T=3M | T=6M | T=0 | T=1M | T=3M | T=6M |
| Buffer 14 | 8 | 10 | 12 | 8 | 8 | 8 | 10 | 8 |
| Buffer 3 | >15 | >15 | >15 | >15 | >15 | >15 | >15 | >15 |
| Buffer 15 | 9 | 10 | 12 | 5 | 9 | 8 | 10 | 5 |
| Buffer 4 | >15 | >15 | >15 | >15 | >15 | >15 | >15 | >15 |
| Buffer 16 | >15 | 10 | 12 | 7 | >15 | 14 | 10 | 9 |

FIG.15A

| Buffer Code | Shake Test Time (min) at 25 °C | | | | | |
|---|---|---|---|---|---|---|
| | F/T | | | LYO | | |
| | T=1M | T=3M | T=6M | T=1M | T=3M | T=6M |
| Buffer 14 | 10 | 7 | 8 | 8 | 12 | 8 |
| Buffer 3 | >15 | >15 | >15 | >15 | >15 | >15 |
| Buffer 15 | 10 | 7 | 5 | 8 | 12 | 5 |
| Buffer 4 | >15 | >15 | >15 | >15 | >15 | >15 |
| Buffer 16 | 10 | 7 | 7 | 10 | 12 | 7 |

FIG.15B

| Buffer Code | Shake Test Time (min) at 37 °C | | | |
|---|---|---|---|---|
| | F/T | | LYO | |
| | T=1M | T=3M | T=1M | T=3M |
| Buffer 14 | 10 | 6 | 8 | 8 |
| Buffer 3 | >15 | >15 | >15 | >15 |
| Buffer 15 | 10 | 6 | 8 | 8 |
| Buffer 4 | >15 | >15 | >15 | >15 |
| Buffer 16 | 10 | 6 | 10 | 8 |

FIG.15C

| Buffer Code | Shake Test Time (min) at −70 °C | |
|---|---|---|
| | F/T | LYO |
| | T=6M | T=6M |
| Buffer 14 | 8 | 8 |
| Buffer 3 | >15 | >15 |
| Buffer 15 | 5 | 5 |
| Buffer 4 | >15 | >15 |
| Buffer 16 | 7 | 9 |

FIG.15D

HPV VACCINE FORMULATIONS COMPRISING ALUMINUM ADJUVANT AND METHODS OF PRODUCING SAME

CROSS-REFERENCE TO RELATED APPLICATIONS

This application is a continuation of U.S. Ser. No. 14/126,992, filed Dec. 17, 2013, which is a §371 National Stage Application of PCT/US2012/43694, international filing date of Jun. 22, 2012, which claims the benefit of U.S. Provisional Application Ser. No. 61/500,829, filed Jun. 24, 2011, now expired, the contents of which are herein incorporated by reference in their entirety.

FIELD OF THE INVENTION

The invention provides human papillomavirus (HPV) antigen formulations which show increased antigen stability post freezing and/or lyophilization. More specifically, the invention provides stable HPV vaccine formulations comprising HPV virus-like particles (VLPs) bound to an aluminum salt adjuvant and methods of producing same.

BACKGROUND OF THE INVENTION

Co-administration of vaccines with compounds that can enhance the immune response against the antigen of interest, known as adjuvants, has been extensively studied. In addition to increasing the immune response against the antigen of interest, some adjuvants may be used to decrease the amount of antigen necessary to provoke the desired immune response or decrease the number of injections needed in a clinical regimen to induce a durable immune response and provide protection from disease.

Aluminum-based compounds were determined to possess adjuvant activity over 60 years ago (for review, see Lindblad, E. B. *Immunol. and Cell Biol.* 82: 497-505 (2004); Baylor et al. *Vaccine* 20: S18-S23 (2002)). Aluminum adjuvants are generally regarded as safe when used at appropriate dosages. Due in part to their low cost and long history of use in human patients, aluminum salt adjuvants are the most prevalent adjuvants used in human vaccines.

Aluminum salt adjuvanted vaccines are typically formulated as liquids which are extremely sensitive to temperature changes, such as heating or freezing. Freezing aluminum-salt containing vaccines causes irreversible damage to the physical structure of the aluminum salt, which results from adjuvant particle agglomeration. This leads to loss of adjuvant activity and, ultimately, a loss of vaccine potency. For this reason, such vaccine formulations must be maintained within a narrow temperature range, preferably between 2° C. and 8° C., which requires a robust cold chain during vaccine transportation and storage. Maintenance of the cold chain is not always economically feasible, especially in developing countries. Additionally, accidental freezing of aluminum salt adjuvanted vaccines is a common problem in both developing and developed countries (Clapp et al., *J Pharm. Sci.* 100(2): 388-401 (2011); Matthias et al., *Vaccine* 25(20): 3980-86 (2007)). Frozen vaccine shipments must be discarded at an enormous cost. Also of concern is the potential for previously frozen, lower potency vaccine to be inadvertently given to patients, leading to decreased efficacy.

Several approaches have been proposed to address the problems associated with maintaining the proper temperature for aluminum salt containing vaccines. One potential solution is to prevent freezing through the addition of formulation components such as propylene glycol, polyethylene glycol or glycerol (Braun, L. J. et al., *Vaccine* 27: 4609-4614 (2009); Braun et al., *Vaccine* 27: 72-79 (2009)). Braun et al., supra, have shown that propylene glycol can prevent freeze-induced adjuvant agglomeration in certain vaccines, even at concentrations too low to prevent freezing.

The use of freeze-dried instead of liquid vaccine formulations may alleviate some issues associated with transportation and storage of a vaccine; however, the process of freeze-drying is also associated with adjuvant particle aggregation and loss of potency (Maa et al., *J. Pharm. Sci.* 92(2): 319-332 (2003)). Clausi et al. (*J. Pharm. Sci.* 97: 2049-61 (2008)) and Randolph et al. (WO 2008/118691) have shown that aluminum adjuvant aggregation during freezing and lyophilization can be mitigated through the addition of high concentrations (e.g. 15%) of trehalose to the formulation. Wolff et al. (*Colloids & Surfaces A: Physiochem Eng. Aspects* 330: 116-126 (2008)) also suggest the use of high concentrations of trehalose to protect aluminum containing vaccines from cold stress. Also proposed by Wolff et al. as candidate formulation components for preventing aluminum adjuvant aggregation were PVP K 25, HES 450 and 200, saccharose and sorbitol. Mizuno et al. (EP Patent No. 0 130 619 B1) propose the use of at least one amino acid or salt thereof in combination with at least one saccharide and at least one colloidal substance.

It would be useful to develop liquid vaccine formulations wherein the vaccine antigen is adsorbed onto an aluminum adjuvant, wherein the formulation is able to retain its physical and immunological properties upon freezing or lyophilizing.

SUMMARY OF THE INVENTION

The invention provides human papillomavirus (HPV) antigen formulations which show increased antigen stability. More specifically, the invention provides stable HPV vaccine formulations comprising HPV virus-like particles (VLPs) of at least one HPV type which are adsorbed onto an aluminum salt adjuvant and further comprise a combination of sucrose and mannitol and optionally, a salt. The vaccine formulations of the invention are stable following freeze-thaw and freeze-drying. Also provided are lyophilized and frozen HPV vaccine formulations comprising HPV VLPs of at least one HPV type adsorbed onto an aluminum salt adjuvant, sucrose, and mannitol.

The invention also relates to an HPV formulation as described above wherein the formulation comprises: (a) HPV VLPs of at least one HPV type adsorbed on an aluminum adjuvant, wherein the VLPs of each HPV type are present in a concentration of 10-200 mcg/ml and wherein the VLPs are selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; and (b) about 1% to about 10% w/v mannitol; and about 0.5% to about 10% sucrose. The formulations of the invention may also comprise additional components including, but not limited to, salt, histidine, and a surfactant. The invention also provides frozen or freeze-dried HPV vaccine formulations as described herein.

Methods of making the stable vaccine formulations of the invention are also provided. To that end, the invention provides a method for producing a stable frozen HPV vaccine formulation comprising: (a) formulating a liquid HPV vaccine formulation comprising (i) HPV VLPs of at least one HPV type adsorbed onto an aluminum salt adjuvant, wherein the VLPs of at least one HPV type are present in a concentration of 10-200 mcg/ml and wherein the VLPs are selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; (ii) about 1% to about 10% w/v mannitol; and (iii) about 0.5% to about 10% sucrose; and (b) freezing the liquid formulation to produce a frozen vaccine formulation. Additional embodiments of the methods of the invention are provided wherein the frozen formulation is dried to produce a lyophilized formulation.

As used throughout the specification and in the appended claims, the singular forms "a," "an," and "the" include the plural reference unless the context clearly dictates otherwise.

As used throughout the specification and appended claims, the following definitions and abbreviations apply:

The term "SWFI" refers to sterile water for injection.

The term "BWFI" refers to bacteriostatic water for injection, which is sterile water comprising an antimicrobial preservative.

The term "API" refers to an active pharmaceutical ingredient, e.g. HPV VLPs, which is a component of the formulations disclosed herein that is biologically active (i.e. capable of inducing an appropriate immune response) and confers a therapeutic or prophylactic benefit to a person or animal in need thereof. As used herein, an API is a vaccine active ingredient.

"Formulation" refers to a composition containing an active pharmaceutical or biological ingredient, along with one or more addition components. The term "formulation" is used interchangeably with the terms "pharmaceutical composition," "vaccine composition," and "vaccine formulation" herein. The formulations can be liquid or solid (e.g., lyophilized). Additional components that may be included as appropriate include pharmaceutically acceptable excipients, additives, diluents, buffers, sugars, amino acids (such as glycine, glutamine, asparagine, arginine or lysine), chelating agents, surfactants, polyols, bulking agents, stabilizers, lyoprotectants, solubilizers, emulsifiers, salts, adjuvants, tonicity enhancing agents (such as alkali metal halides, preferably sodium or potassium chloride, mannitol, sorbitol), delivery vehicles and anti-microbial preservatives.

Acceptable formulation components for pharmaceutical preparations are nontoxic to recipients at the dosages and concentrations employed. Typically, the "formulation" is a single dose of API, which can be delivered to a single patient or animal in need thereof. The term "multi-dose" refers to a formulation which contains more than one dose of an API which can be administered to a patient more than one time. A multi-dose formulation typically comprises an anti-microbial preservative. The term "formulation" is used interchangeably herein with the terms "composition," "biological composition," and "pharmaceutical composition."

The term "cake" refers to a dry pellet that results when a liquid formulation has been lyophilized or freeze-dried, as described herein. The appearance of the cake is partially indicative of the impact of the lyophilization process on the properties of the lyophilized formulation. As used herein, "dry cake" refers to a cake that comprises about 20% or less residual moisture content. In some embodiments of the invention, the moisture content of the dry cake is 15% or less, 10% or less, or 5% or less. In alternative embodiments, the moisture content of the dry cake is within a range of about 0.1% to about 10%, about 0.1% to about 6%, about 0.5% to about 10% or 0.5% to about 6%.

The term "reconstitution time" refers to the time that is required to rehydrate a dry, lyophilized, formulation (cake) so that the resulting reconstituted liquid formulation is clarified and the cake has been dissolved.

The term "therapeutically effective amount" refers to an amount of the active ingredient (i.e. therapeutic protein or antibody) sufficient to produce the desired therapeutic effect in a human or animal, e.g. the amount necessary to treat, cure, prevent, or inhibit development and progression of disease or the symptoms thereof and/or the amount necessary to ameliorate symptoms or cause regression of disease. Such a therapeutically effective amount may vary depending on the structure and potency of the active ingredient and the contemplated mode of administration. One of skill in the art can readily determine a therapeutically effective amount of a given antibody or protein.

The term "treatment" refers to both therapeutic treatment and prophylactic or preventative measures. Those in need of treatment include those individuals, such as humans and animals, already with the disorder or condition to be treated as well as those prone to have the disorder or those in which the disorder is to be prevented. As used herein, "treatment" also includes reduction of the likelihood of obtaining the disorder, reduction of the severity of the disorder in those already afflicted, and the induction of regression of the disorder or symptoms thereof.

A "pharmaceutically-acceptable carrier" means a liquid filler, diluent or encapsulating substance that may be safely used in systemic administration. Depending upon the particular route of administration, a variety of pharmaceutically acceptable carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions including phosphate buffered saline, emulsifiers, isotonic saline, and pyrogen-free water. In particular, pharmaceutically acceptable carriers may contain different components such as a buffer, sterile water for injection, normal saline or phosphate-buffered saline, sucrose, histidine, salts and polysorbate. Terms such as "physiologically acceptable", "diluent" or "excipient" can be used interchangeably.

Additional abbreviations employed herein include the following: FAP=frozen aqueous product, form.=formulation; F/T=freeze-thaw; 1× Normal F/T=1× freeze-thaw, as described in Example 1, 3× Normal F/T=3× freeze-thaw, as described in Example 1, 1× Flash F/T=flash freeze-thaw, as described in Example 1 (also referred to herein as F/T FF 1×), His=histidine; HPV=human papillomavirus; hr.=hour(s); lyo=lyophilization or lyophilized, as dictated by the context; min.=minute(s); mM=millimolar; PS20=Polysorbate 20; PS80=Polysorbate 80; recon.=reconstitution; sec.=second(s), DLS=Dynamic Light Scattering; NaCl=sodium chloride; vol.=volume; VLP=virus-like particle; WFI=water for injection; w/v=weight per volume.

BRIEF DESCRIPTION OF THE DRAWINGS

FIG. 1 shows the compositions of buffers used in the freeze-thaw and lyophilization studies described herein. There were 6 buffers (Buffer A through Buffer F) and 3 variations of each buffer comprising varying amounts of salt (0, 150 and 320 mM sodium chloride), as shown, resulting in 18 different buffer compositions (B-1 through B-18). In addition to the excipients listed, each of the buffers contained 10 mM histidine and 0.01% Polysorbate 80, pH 6.2.

FIG. 7 shows the cake appearance for lyophilized 4-valent HPV formulations in various buffers (Buffer A through Buffer F) comprising 0, 150 or 320 mM sodium chloride. Formulations were lyophilized with flash freezing ("Flash freeze") or lyophilized on a pre-cooled lyophilization shelf ("Pre-cooled"). Results provided represent the average of 3 vials for each test formulation at the T=0 time point. Cake appearances of the same formulations following storage for 1 month at 45° C. are also shown. See Example 1, Table 2, for a description of quality attributes for the dried cakes. See Example 5.

FIG. 8 provides the reconstitution time for lyophilized 4-valent HPV formulations in various buffers (Buffer A though Buffer F) comprising 0, 150 or 320 mM sodium chloride following addition of sterile water for injection. Formulations were lyophilized with flash freezing ("Flash freeze") or lyophilized on a pre-cooled lyophilization shelf ("Pre-cooled"). Results provided are for 2 vials for each test formulation. Reconstitution times following addition of sterile water for injection for the same formulations following storage for 1 month at 45° C. are also shown. See Example 5.

FIG. 9 provides the shake test time for lyophilized 4-valent HPV formulations in various buffers (Buffer-A through Buffer-F) comprising 0, 150 or 320 mM sodium chloride following addition of sterile water for injection. Formulations were lyophilized with flash freezing ("Flash freeze") or lyophilized on a pre-cooled lyophilization shelf ("Pre-cooled"). Results provided are for 3 vials for each test formulation. See Example 5.

FIGS. 13A-13D show the cake appearance for lyophilized 4-valent HPV formulations (Buffer B through Buffer D) following storage for several months at various storage temperatures. Results provided represent the average of 3 vials for each test formulation. See Example 1, Table 2, for a description of quality attributes for the dried cakes. See Example 10. Data are provided for storage at 2-8° C. (FIG. 13A), 25° C. (FIG. 13B), 37° C. (FIG. 13C) and −70° C. (FIG. 13D).

FIGS. 14A-14D show the cake appearance for lyophilized 1×MAA formulations (Buffer B through Buffer D) following storage for several months at various storage temperatures. Results provided represent the average of 3 vials for each test formulation. See Example 1, Table 2, for a description of quality attributes for the dried cakes. See Example 10. Data are provided for storage at 2-8° C. (FIG. 14A), 25° C. (FIG. 14B), 37° C. (FIG. 14C) and −70° C. (FIG. 14D).

FIGS. 15A-15D provide the shake test time for lyophilized 4-valent HPV formulations (Buffer B through Buffer D) following storage for several months at various storage temperatures. Results provided are for 3 vials for each test formulation. See Example 10. Data are provided for storage at 2-8° C. (FIG. 15A), 25° C. (FIG. 15B), 37° C. (FIG. 15C) and −70° C. (FIG. 15D).

DETAILED DESCRIPTION OF THE INVENTION

Figure 2A:
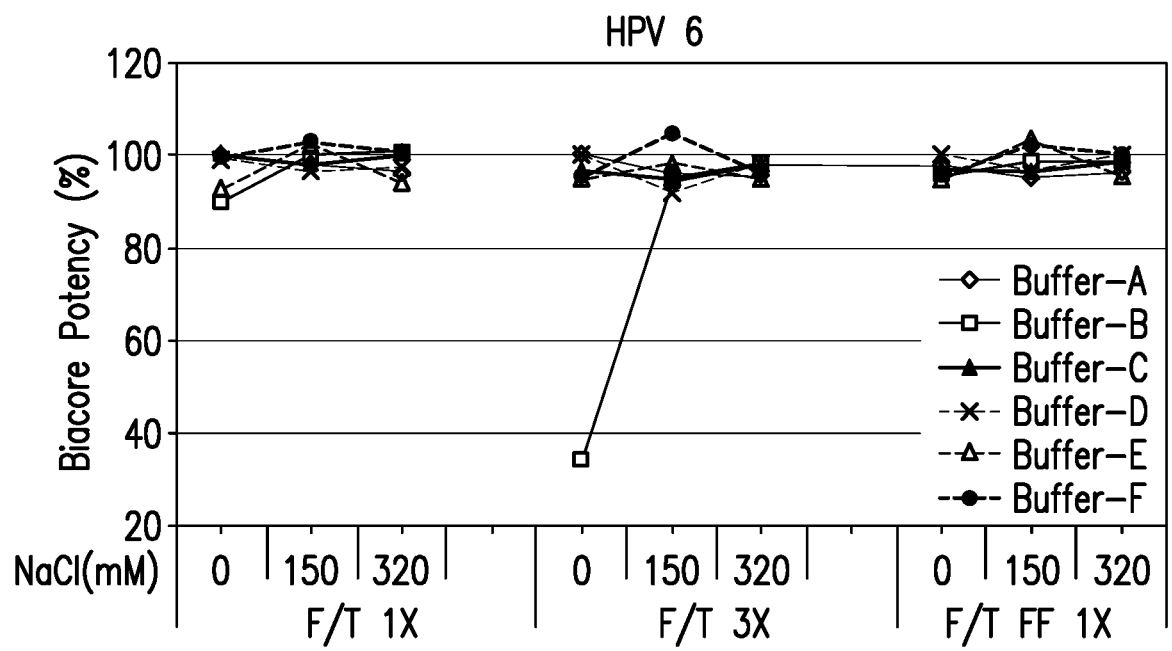
FIGS. 2A-2D show plots of the in vitro antigenicity data for each of the HPV types in the 4-valent test formulations as a function of sodium chloride concentration and freeze thaw conditions for each test buffer (Buffer A through Buffer F). See Example 2. Plots are provided for HPV type 6 (FIG. 2A), HPV type 11 (FIG. 2B), HPV type 16 (FIG. 2C), and HPV type 18 (FIG. 2D). HPV vaccine formulations were subjected to either fast flash freezing using liquid nitrogen blast one time ("F/T FF 1×") or normal freezing either one time ("F/T 1×") or 3 times ("F/T 3×"), as described in Example 1.
Figure 2B:
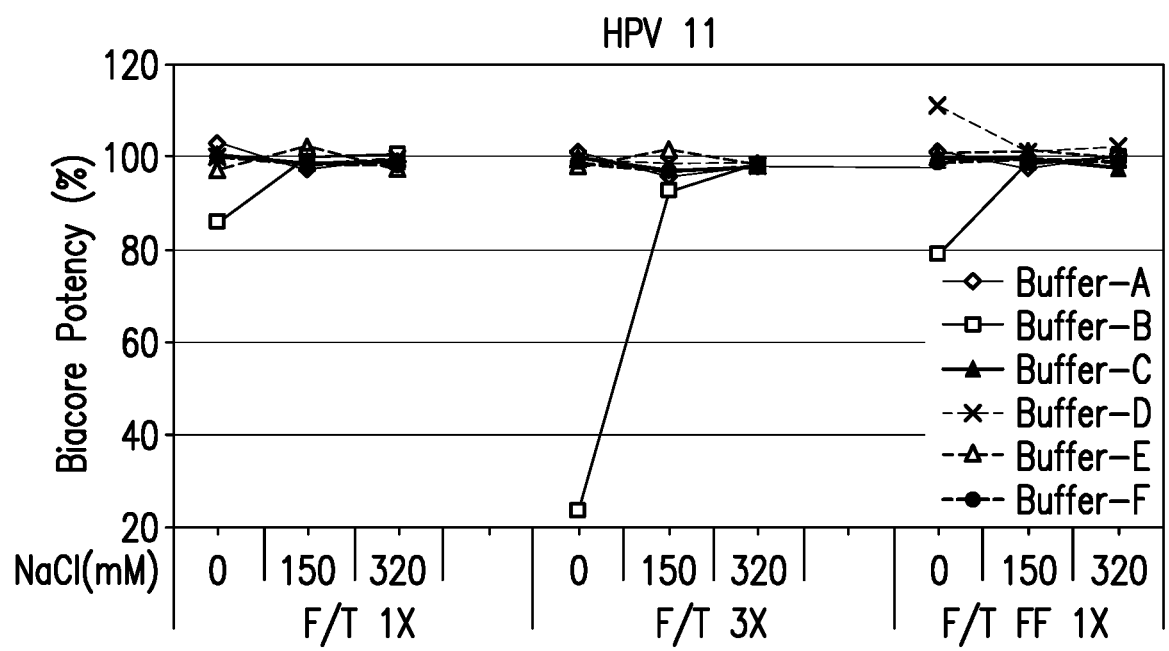
Figure 2C:
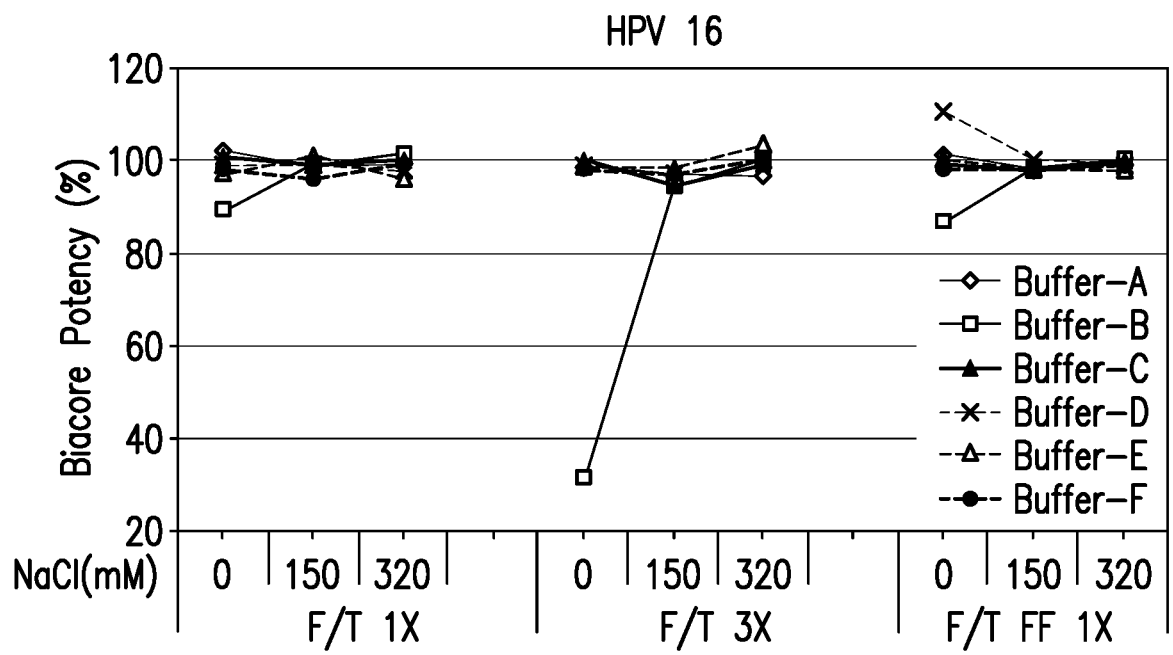
Figure 2D:
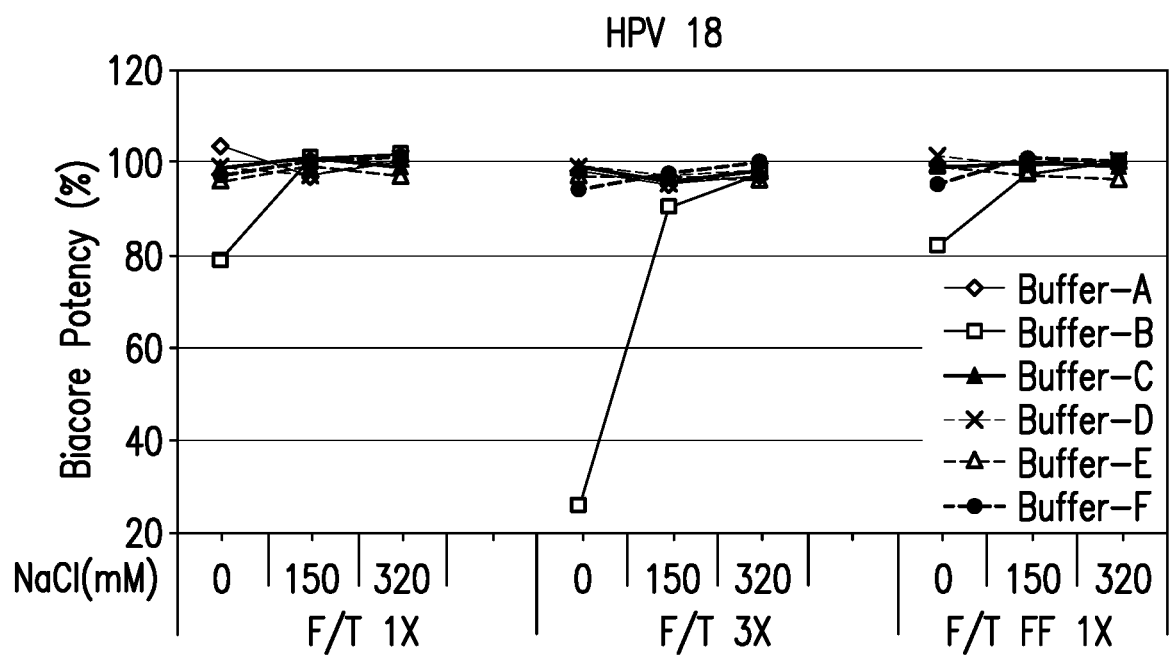
Figure 3A:
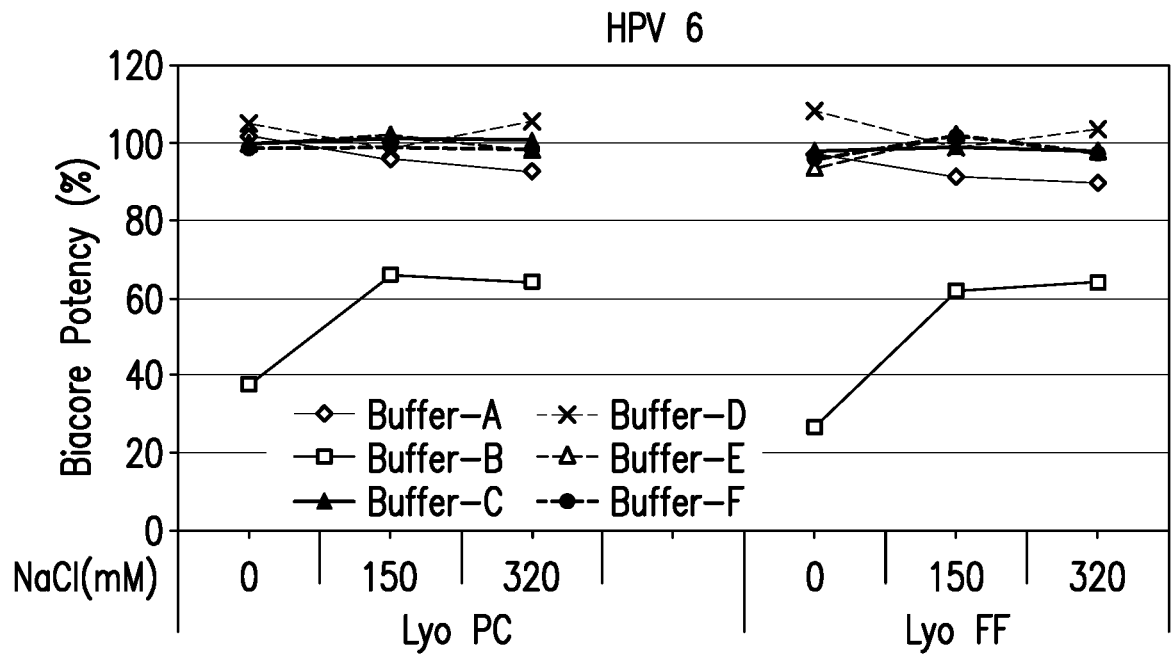
FIGS. 3A-3D show plots of in vitro antigenicity data for each of the HPV types in the 4-valent test formulations as a function of sodium chloride concentration following lyophilization. See Example 2. Results are shown for HPV type 6 (FIG. 3A), HPV type 11 (FIG. 3B), HPV type 16 (FIG. 3C) and HPV type 18 (FIG. 3D) in the 4-valent HPV formulations comprising Buffer A through Buffer F. Each of the compositions was subjected to lyophilization with freezing done either by flash freezing ("Lyo FF") using liquid nitrogen blast or using a pre-cooled lyophilization shelf ("Lyo PC"), as described in Example 1.
Figure 3B:
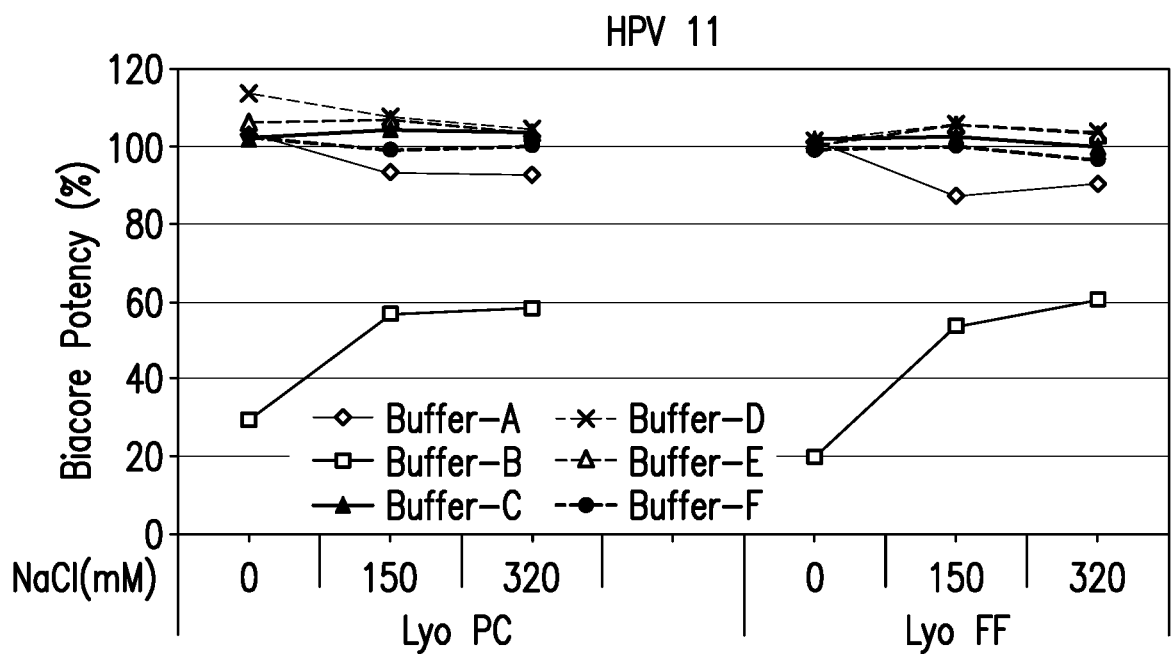
Figure 3C:
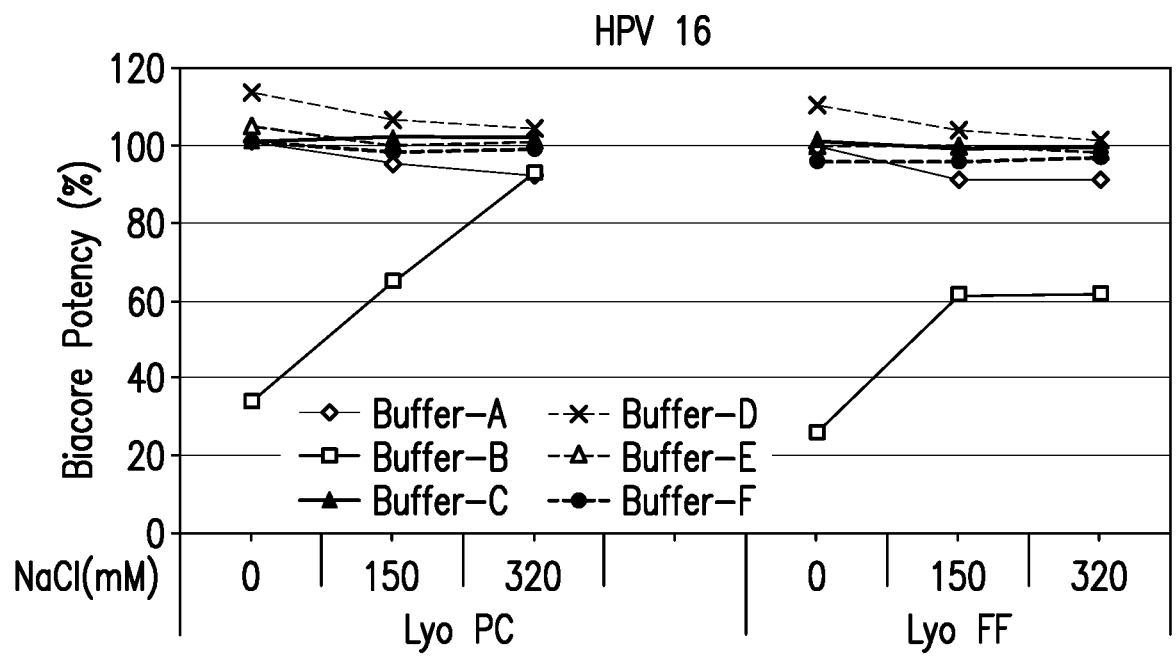
Figure 3D:
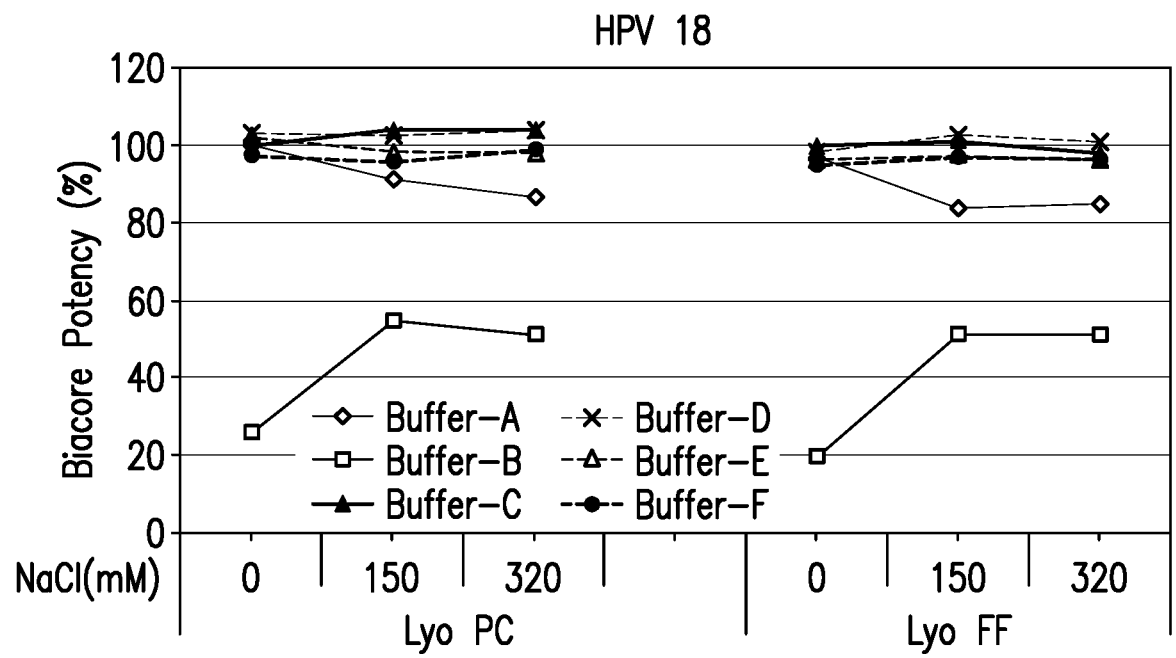
Figure 4A:
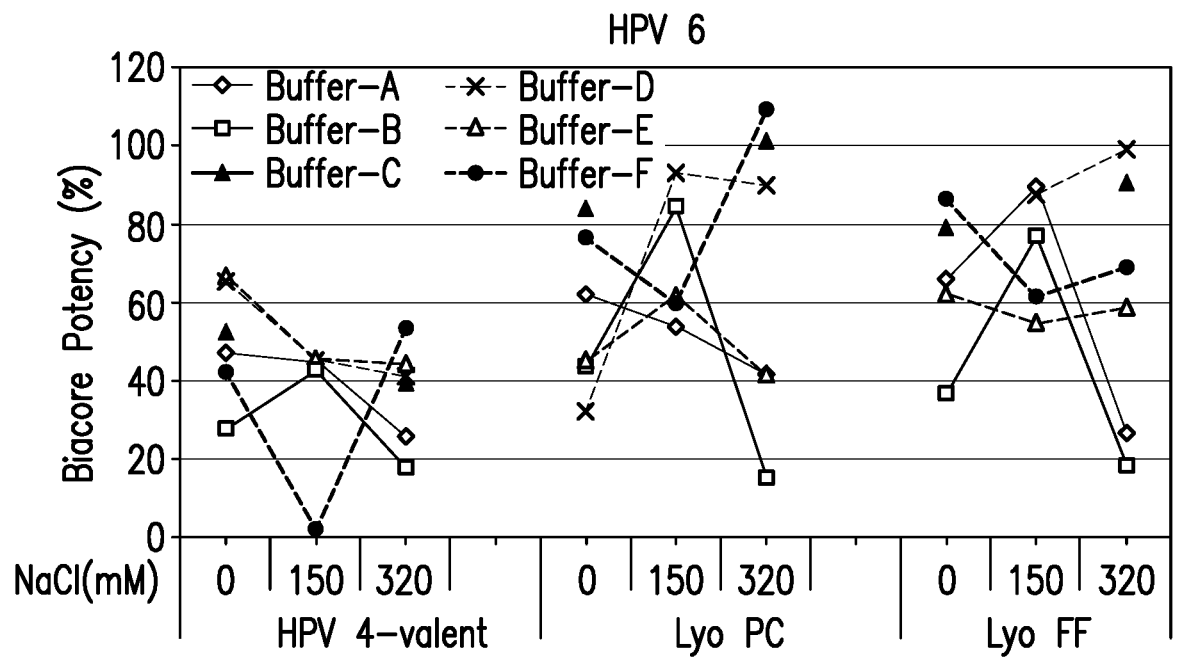
FIGS. 4A-4D show plots of in vitro antigenicity for each of the HPV types as a function of sodium chloride concentration and lyophilization conditions in various buffer compositions after storage for 1 month at 45° C. (HPV 6 (FIG. 4A), HPV 11 (FIG. 4B), HPV16 (FIG. 4C) and HPV 18 (FIG. 4D)). Also included are the respective non-lyophilized liquid formulations that were subjected to storage for 1 month at 45° C. The data provided are for the same test formulations, under the same conditions as those shown in FIG. 2, following storage for 1 month at 45° C.
Figure 4B:
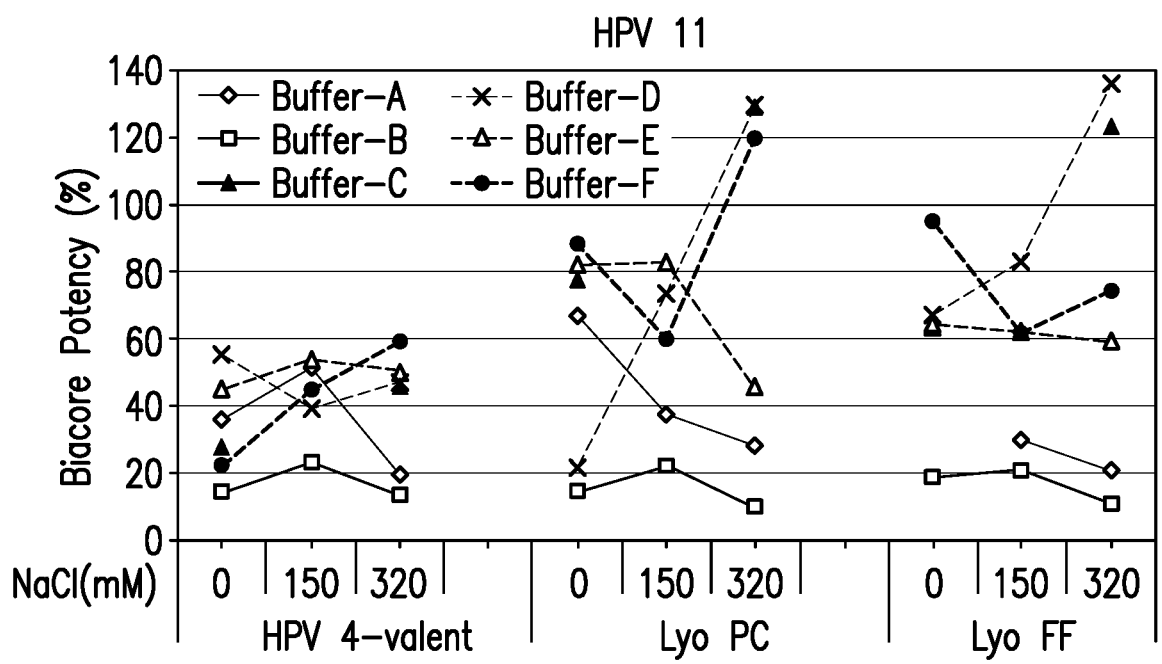
Figure 4C:
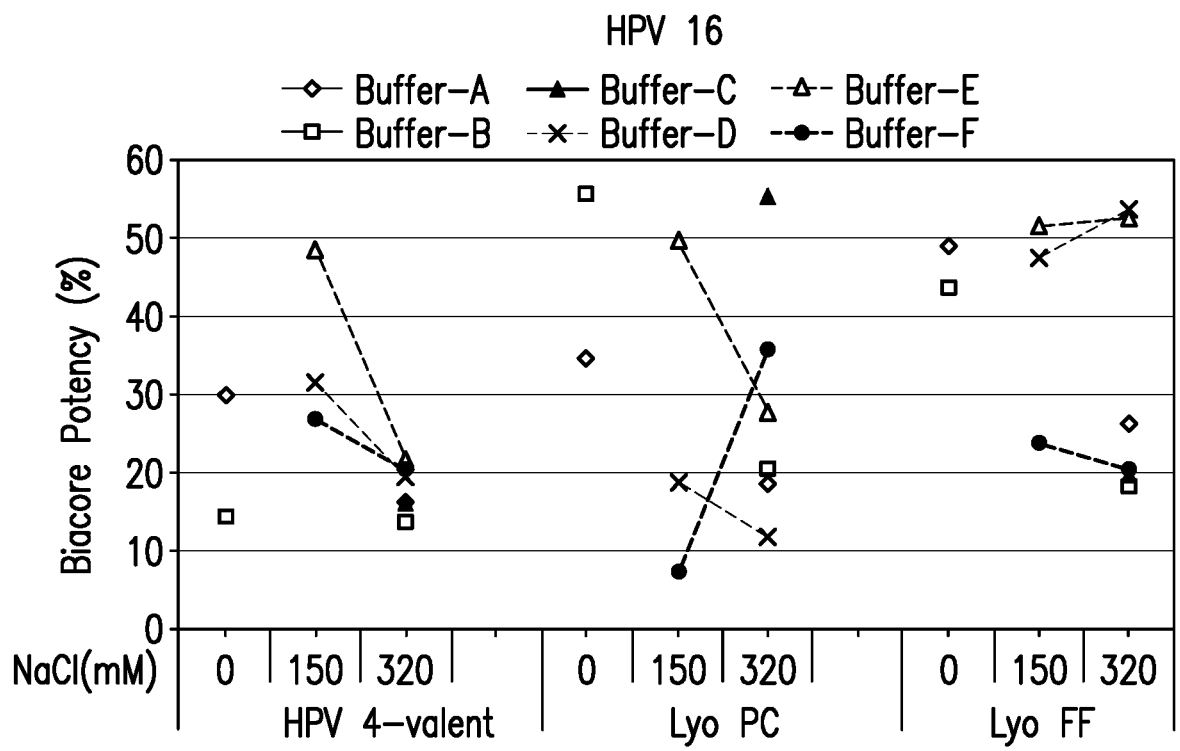
Figure 4D:
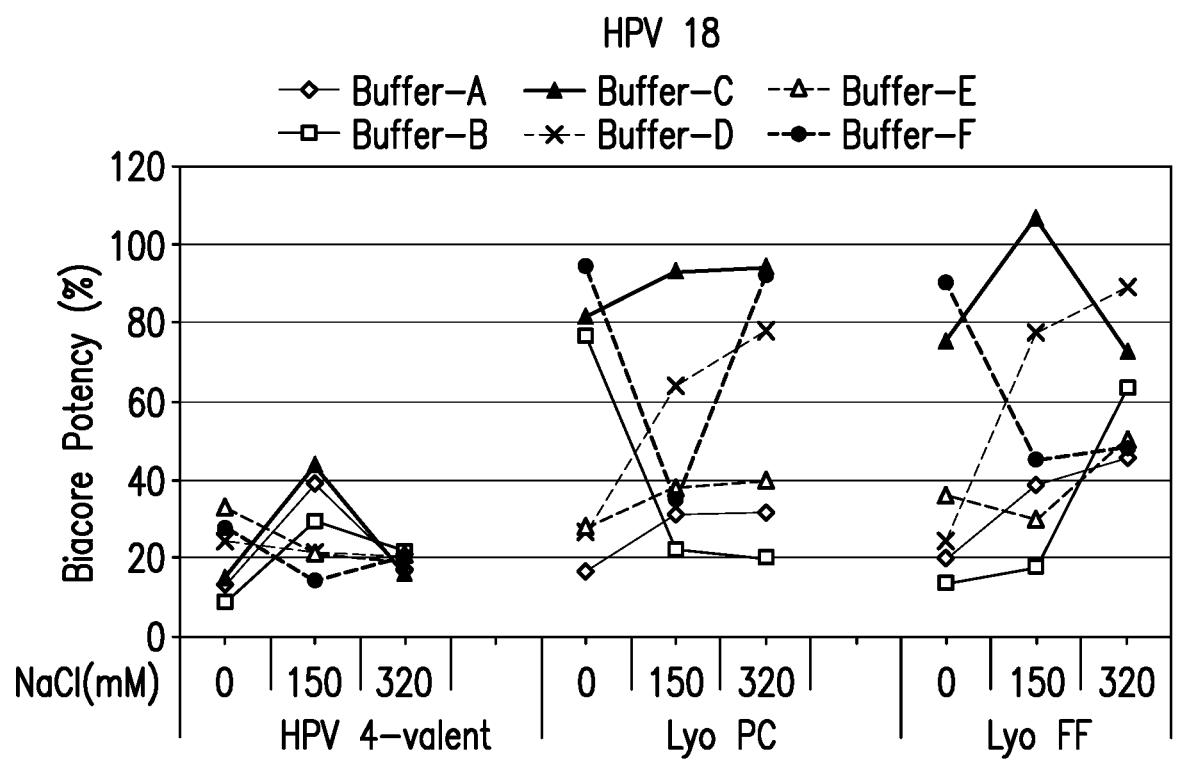

Vaccine formulations commonly contain aluminum adjuvants, which are used to boost the immune response to the antigen. Aluminum adjuvanted vaccines are extremely sensitive to temperature changes, such as heating or freezing. To avoid issues of decreased potency and/or efficacy as described above, there is a need for methods of producing thermally stable vaccine formulations comprising an aluminum salt adjuvant that are immunologically active. To that end, the present invention provides stable liquid and solid frozen and freeze-dried vaccine formulations which comprise at least one antigen adsorbed onto an aluminum salt adjuvant and a combination of mannitol and sucrose. In preferred aspects of the invention, the antigen is a human papillomavirus (HPV) virus-like particle (VLP).

As stated above, the present invention provides a human papillomavirus vaccine formulation comprising (a) HPV virus-like particles (VLPs) of at least one HPV type which are adsorbed onto an aluminum adjuvant; and (b) a buffer comprising mannitol and sucrose. The vaccine formulations optionally comprise a non-ionic surfactant and/or a salt such as NaCl.

Liquid HPV vaccine formulations in accordance with the invention are capable of retaining their physical and immunological characteristics upon (1) freezing and thawing; (2) freeze-drying the liquid formulation; (3) reconstituting the dried formulation and (4) reconstituting the dried formulation following storage for one month or more at room temperature or an elevated temperature. Accordingly, the invention provides an HPV vaccine formulation as described throughout the specification in varying embodiments, which is frozen, freeze-dried or reconstituted.

In preferred embodiments of this aspect of the invention, the HPV vaccine formulation comprises (a) HPV virus-like particles (VLPs) of at least one HPV type adsorbed on an aluminum adjuvant, wherein the VLPs of each HPV type are present in a concentration of 10-200 mcg/ml and wherein the VLPs are selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; (b) about 1% to about 10% w/v mannitol; and (c) about 0.5% to about 10% sucrose. In additional embodiments, the HPV vaccine formulation further comprises a non-ionic surfactant. In a further embodiment, the vaccine formulation comprises components as defined in any preceding embodiment and further comprises a salt.

Additional embodiments of the invention provide an HPV formulation as defined above, wherein the amount of mannitol present in the formulation is from about 4% to about 10% and the amount of sucrose is from about 1% to about 5%.

Further embodiments of this aspect of the invention are provided wherein the formulation comprises components as defined in any preceding formulation and further comprises about 5 mM to about 100 mM histidine. In preferred embodiments, the formulation comprises 10 mM histidine.

In additional embodiments, the invention relates to an HPV vaccine formulation as defined in any preceding embodiment, wherein the formulation additionally comprises a surfactant. In exemplary embodiments of the invention, the vaccine formulation comprises about 0.001% to about 0.04% surfactant. In some embodiments the surfactant is PS20 or PS80.

In yet another embodiment of this aspect of the invention, the HPV vaccine formulation comprises HPV VLPs of at least one HPV type adsorbed onto an aluminum salt adjuvant, wherein the VLPs of at least one HPV type are present in a concentration of 10-200 mcg/ml and wherein the VLPs are selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; (b) about 5% to about 6% w/v mannitol; and (c) about 2% to about 4% sucrose. In a further embodiment, the vaccine formulation further comprises about 10 mM histidine, about 0.30 to about 0.35M NaCl and/or 0.01% PS80.

Formulation Components

As noted above, in accordance with the invention it has been shown that a combination of mannitol and sucrose protects aluminum adjuvanted vaccine formulations from stress induced by freezing, thawing or freeze-drying. To that end, the invention provides vaccine formulations, e.g. HPV VLP vaccine formulations, wherein the formulation components are as defined in any of the preceding embodiments and mannitol is present in any of the following amounts: about 1% to about 10% w/v, about 2% to about 10% w/v, about 3% to about 10% w/v, about 4% to about 10% w/v, about 5% to about 10% w/v, about 1% to about 9% w/v, about 2% to about 9% w/v, about 3% to about 9% w/v, about 4% to about 9% w/v, about 5% to about 9% w/v about 1% to about 8% w/v, about 2% to about 8% w/v, about 3% to about 8% w/v, about 4% to about 8% w/v, about 5% to about 8% w/v, about 1% to about 7% w/v, about 2% to about 7% w/v, about 3% to about 7% w/v, about 4% to about 7% w/v, about 1% to about 6% w/v, about 2% to about 6% w/v, about 3% to about 6% w/v, or about 4% to about 6% w/v. In alternative embodiments of the invention, the vaccine formulation components are as described in any preceding embodiment and the amount of mannitol is 1%, 2%, 3%, 4%, 5%, 6%, 7%, 8%, 9% or 10% w/v. In preferred embodiments, the compositions comprise 4%, 5%, or 6% w/v mannitol.

In further embodiments of the invention, the HPV vaccine formulation comprises components as defined in any of the preceding embodiments and sucrose in any of the following amounts: about 0.5% to about 10% w/v, about 1% to about 10% w/v, about 2% to about 10% w/v, about 3% to about 10% w/v, about 4% to about 10% w/v, about 0.5% to about 9% w/v, about 1% to about 9% w/v, about 2% to about 9% w/v, about 3% to about 9% w/v, about 4% to about 9% w/v, about 1% to about 8%, about 2% to about 8%, about 3% to about 8%, about 4% to about 8%, about 1% to about 7%, about 2% to about 7%, about 3% to about 7%, about 4% to about 7%, about 1% to about 6%, about 2% to about 6%, about 3% to about 6%, about 4% to about 6% w/v sucrose. In alternative embodiments, the vaccine composition comprises 0.5%, 1%, 2%, 3%, 4%, 5%, 6%, 7%, 8%, 9% or 10% w/v sucrose. In preferred embodiments, the compositions comprise 2%, 3%, 4% or 5% w/v sucrose.

In specific embodiments of the invention, the HPV vaccine formulations comprise components as defined in any preceding embodiment or any embodiment described below, and further comprise about 5 mM to about 100 mM histidine. In additional embodiments, the concentration of histidine in the composition is about 5 mM to about 90 mM, about 5 mM to about 80 mM, about 5 mM to about 75 mM, about 5 mM to about 60 mM, about 5 mM to about 50 mM, about 10 mM to about 90 mM, about 10 mM to about 75 mM, about 10 to about 60 mM, about 10 mM to about 50 mM, about 20 mM to about 90 about, about 20 mM to about 75 mM, about 20 to about 60 mM, or about 20 mM to about 50 mM. In alternative embodiments, the vaccine composition comprises about 5 mM, about 10 mM, about 20 mM, about 30 mM, about 40 mM or about 50 mM histidine. In one preferred embodiment, the vaccine formulation comprises about 10 mM histidine.

Any of the vaccine compositions described herein may optionally comprise a surfactant. Surfactants may be added to reduce and/or prevent aggregation or to prevent and/or inhibit protein damage during processing conditions such as purification, filtration, freeze-drying, transportation, storage, and delivery. Surfactants that are useful in the formulations of the invention include, but are not limited to: nonionic surfactants such as polyoxyethylene sorbitan fatty acid esters (Polysorbates, sold under the trade name Tween® (Uniquema Americas LLC, Wilmington, Del.)) including Polysorbate-20 (polyoxyethylene sorbitan monolaurate), Polysorbate-40 (polyoxyethylene sorbitan monopalmitate), Polysorbate-60 (polyoxyethylene sorbitan monostearate), and Polysorbate-80 (polyoxyethylene sorbitan monooleate); polyoxyethylene alkyl ethers such as Brij® 58 (Uniquema Americas LLC, Wilmington, Del.) and Brij® 35; poloxamers (e.g., poloxamer 188); Triton® X-100 (Union Carbide Corp., Houston, Tex.) and Triton® X-114; NP40; Span 20, Span 40, Span 60, Span 65, Span 80 and Span 85; copolymers of ethylene and propylene glycol (e.g., the Pluronic® series of nonionic surfactants such as Pluronic® F68, Pluronic® 10R5, Pluronic® F108, Pluronic® F127, Pluronic® F38, Pluronic® L44, Pluronic® L62 (BASF Corp., Ludwigshafen, Germany); and sodium dodecyl sulfate (SDS).

In exemplary embodiments of the invention, the surfactant is a nonionic surfactant selected from the group consisting of: Polysorbate 20, Polysorbate 80, Brij®35, Pluronic® F-68 and Triton®. In some preferred embodiments, the surfactant is Polysorbate 20 or Polysorbate 80.

The amount of surfactant to be included in the formulations of the invention is an amount sufficient to perform the desired function, i.e. a minimal amount necessary to prevent protein aggregation, to prevent or inhibit the formation of particulates, to reduce the amount of aggregation of the lyophilized or frozen formulation or reconstituted formulation after addition of diluent such as BWFI to an acceptable level, to allow ease of reconstitution or to provide a stability advantage during shipping and/or processing. Typically, the surfactant is present in a concentration of from about 0.001% to about 0.5% (wt/vol). In preferred embodiments of this aspect of the invention, the surfactant is present in the formulation (prior to lyophilization) in an amount from about 0.005% to about 0.4%; in more preferred embodiments, the surfactant is present in an amount from about 0.01% to about 0.3%. In particularly preferred embodiments, the surfactant is present in an amount of about 0.01%.

In exemplary embodiments of the invention, the surfactant is a nonionic surfactant selected from the group consisting of: Polysorbate 20, Polysorbate 80, Brij®35, Pluronic® F-68 and Triton®. In some preferred embodiments, the surfactant is Polysorbate 20 or Polysorbate 80. In particularly preferred embodiments, the HPV vaccine formulation comprises about 0.01% PS80.

The invention also includes vaccine formulations which comprise components as defined in any preceding embodiment and further comprise a salt, which can contribute to the control of the ionic strength of the formulation. Salts that can be used in the HPV vaccine formulations of the invention include, but are not limited to, NaCl, KCl, $Na_2SO_4$, $(NH_4)_2SO_4$, sodium phosphate and sodium citrate. The salt should be present in the formulation in a concentration of from about 0.10M to 1M. However, very high concentrations are not preferred due to the practical limitations of parental injection of high salt formulations. Instead, more moderate salt concentrations, such as more physiological concentrations of about 0.15 M to about 0.5 M with 0.15 M-0.32 M NaCl are preferred. In alternative embodiments of the invention, the HPV vaccine formulations do not comprise salt.

The pH of the vaccine compositions of the invention, as described in any preceding embodiment or any embodiment described below, is preferably in the range of about 5.5 to about 7.5. In specific embodiments of the invention, the pH of the composition is about 5.5, about 5.75, about 6.0, about 6.1, about 6.2, about 6.25, about 6.3, about 6.4, about 6.5, about 6.75 about 7.0, about 7.25 or about 7.5. In additional embodiments, the pH is about 5.5 to about 7.0, about 5.5 to about 6.5, about 6.0 to about 7.5, about 6.0 to about 7.0, about 6.5 to about 7.0, about 6.0 to 6.5, about 6.0 to about 6.9, about 6.2 to about 6.75, or about 6.0 to about 6.75.

In some circumstances, it may be desirable to provide a multi-dose HPV vaccine formulation which comprises more than one dose of vaccine in the same vial. If a multi-dose formulation is desired, an anti-microbial preservative should be used to kill or prevent the growth of microorganisms, such as bacteria and fungi. Multi-dose vaccine formulations containing anti-microbial preservatives provide several advantages over single dose formulations, including allowing multiple doses of vaccine to be withdrawn from the vial without the concern that the first withdrawal inadvertently introduced microbial contamination (Meyer et al., *J. Pharm. Sci.* 96(12): 3155-3167 (2007)). Preferred antimicrobial preservatives for use in the HPV vaccine formulations of the invention include an antimicrobial preservative selected from the group consisting of: m-cresol, phenol, and benzyl alcohol (see Bryan et al., U.S. Pat. No. 7,709,010).

The formulations of the invention are preferably stable for at least 1 month at or below room temperature. The stability of the formulation is tested by various methods used to determine the biophysical properties (such as aggregation using a method to measure particle size using dynamic light scattering (DLS) and binding affinities (such as potency assays using Biacore) of the API before and after freezing or lyophilization and/or after storage conditions. In some embodiments of the invention, the formulations are stable for 1 month, 3 months, 6 months, or greater than 6 months at or below room temperature (e.g. 20-25° C.) following lyophilization or freeze-thaw process stress. In further embodiments the formulations are stable for 6 months, over 6 months, or over a year when stored below room temperature (e.g. −70° C. or between 2-8° C.). In still other embodiments, the formulations are stable for over 1 month or 3 months at 37° C. following lyophilization or freeze-thaw process stress. In preferred embodiments, the formulations of the invention are in the vaccine vial monitor (VVM) category VVM30 (i.e. stable for 193 days at 25° C. or 30 days at 37° C.). See Examples for description of VVM system.

It is shown herein that a combination of mannitol and sucrose in the formulations of the invention allow the HPV VLP vaccine compositions to maintain stability at −70° C. or 2-8° C. for greater than 6 months following lyophilization or freeze-thaw procedures. It is also shown that formulations of the invention comprising a combination of mannitol and sucrose maintain their potency for >6 months at 25° C. or 3 months at 37° C. following lyophilization.

The formulations of the present invention may further comprise additional components and pharmaceutically acceptable carriers including, but not limited adjuvants, which may be added to increase the immune response of the patient's immune system to the API (HPV VLPs), a buffer, a stabilizer, a solubilizer, a tonicity modifier, a chelating agent, dextran, dextran sulfate, dextran T40, diethanolamine, guanidine, calcium chloride, sodium citrate, albumin, gelatin, polyethylene glycol (PEG), lipids, and heparin. The skilled artisan is readily able to determine which additional excipients should be included in a desired vaccine formulation, dependant on its function in the formulation, as well as the projected mode of administration, dosage, and other factors such as the expected storage time and temperature of the formulation. The skilled artisan recognizes that the amount of the additional excipients may vary, and can readily determine a proper amount that is both safe for administration to humans or animals and effective for the desired function.

HPV Virus-Like Particles

More than 80 types of HPV have been identified to date, many of which have been associated with pathologies ranging from benign proliferative warts to malignant carcinomas of the cervix (for review, see McMurray et al., *Int. J. Exp. Pathol.* 82(1): 15-33 (2001)). HPV types 6 and 11 are termed "low-risk" and are the HPV types which are most commonly associated with benign warts, nonmalignant condyloma acuminata and/or low-grade dysplasia of the genital or respiratory mucosa. Approximately 90% of genital warts are caused by these two HPV types. In contrast, HPV 16 and HPV 18 are termed "high-risk" HPV types because they are most frequently associated with in situ and invasive carcinomas of the cervix, vagina, vulva and anal canal. More than 70% of cervical carcinomas are caused by infections with HPV16 and HPV18. Together with the less prevalent oncogenic types HPV 31, −33, −45, −52 and −58, these types account for greater than 90% of cervical cancer (Schiffman et al., *J. Natl. Cancer Inst.* 85(12): 958-64 (1993)).

Papillomaviruses are small (50-60 nm), nonenveloped, icosahedral DNA viruses that encode up to eight early (E1-E7) and two late (L1-L2) genes. The L1 protein is the major capsid protein and has a molecular weight of 55-60 kDa. Expression of the L1 protein or a combination of the L1 and L2 proteins in yeast, insect cells, mammalian cells or bacteria leads to self-assembly of virus-like particles (VLPs) (for review, see Schiller and Roden, in *Papillomavirus Reviews: Current Research on Papillomaviruses*; Lacey, ed. Leeds, UK: Leeds Medical Information, pp 101-12 (1996)). VLPs are morphologically similar to authentic virions and are capable of inducing high titres of neutralizing antibodies upon administration into animals or humans. Because VLPs do not contain the potentially oncogenic viral genome, they present a safe alternative to the use of live virus in HPV vaccine development (for review, see Schiller and Hidesheim, *J. Clin. Virol.* 19: 67-74 (2000)). For this reason, the L1 and L2 genes have been identified as immunological targets for the development of prophylactic and therapeutic vaccines for HPV infection and disease.

Accordingly, the vaccine compositions of the present invention comprise HPV VLPs comprised of recombinant L1 or recombinant L1+L2 proteins of at least one type of HPV. HPV L1 or HPV L1+L2 protein can be expressed recombinantly by molecular cloning of L1 or L1+L2 DNA into an expression vector containing a suitable promoter and other appropriate transcription regulatory elements, and transferred into prokaryotic or eukaryotic host cells to produce recombinant protein. Techniques for such manipulations are fully described by Sambrook et al. (*Molecular Cloning: A Laboratory Manual*; Cold Spring Harbor Laboratory, Cold Spring Harbor, N.Y., (1989)), which is hereby incorporated by reference. VLPs can self-assemble when L1 protein is recombinantly expressed in a host cell.

The recombinant HPV L1 proteins of the present invention may be any full-length L1 protein sequence that can be found in nature or any mutated or truncated L1 protein that is capable of self-assembling into VLPs. L1 protein sequences for use in the present invention can be determined by isolating DNA from one or more clinical samples containing an HPV type of choice, determining the sequence of the HPV L1 DNA sequence, and translating the DNA sequence into an amino acid sequence using the genetic code. Many exemplary L1 sequences suitable for use in the present invention can be found in the literature. See, e.g., U.S. Pat. Nos. 5,820,870; 7,250,170; 7,276,243; and U.S. Pat. No. 5,437,951; Kirii et al. (*Virology* 185(1): 424-427 (1991)). Further L1 proteins that are useful in the compositions and formulations of the present invention include biologically active fragments and/or mutants of an HPV L1 sequence, including but not necessarily limited to amino acid substitutions, deletions, additions, amino terminal truncations and carboxy-terminal truncations, such that these mutations provide for L1 proteins or protein fragments that are capable of forming a VLP. See, e.g., International Publication WO 2006/114312 and U.S. Pat. No. 6,599,508.

Appropriate host cells for the expression of recombinant HPV L1 or recombinant L1+L2 and subsequent self-assembly of VLPs include, but are not limited to yeast cells, insect cells, mammalian cells or bacteria. In exemplary embodiments of the invention, the VLPs are produced in yeast cells such as a yeast selected from the group consisting of: *Saccharomyces cerevisiae, Hansenula polymorpha, Pichia pastoris, Kluyvermyces fragilis, Kluveromyces lactis,* and *Schizosaccharomyces pombe*. Expression of HPV VLPs in yeast cells offers the advantages of being cost-effective and easily adapted to large-scale growth in fermenters.

The present invention also includes formulations comprising mutant forms of HPV VLPs, such as HPV VLPs that comprise biologically active fragments and/or mutants of an HPV L1 or L2 protein, including but not necessarily limited to amino acid substitutions, deletions, additions, amino terminal truncations and carboxy-terminal truncations such that these mutations provide for proteins or protein fragments of therapeutic or prophylactic use and would be useful for HPV VLP vaccine development. Any such mutant form of an HPV L1 protein should be capable of forming VLPs and of provoking an immune response against the desired HPV type when administered to a human patient.

Additionally, one of skill in the art will recognize that the L1 or L1+L2 protein, which is used to self-assemble VLPs for inclusion in the formulations disclosed herein, may be encoded by a full-length wild-type HPV L1 or L2 polynucleotide, or may be encoded by a fragment or mutant of the known wild-type sequence. Wild-type polynucleotide sequences that encode mRNA expressing HPV L1 or L2 protein are available in the art. Any mutant polynucleotide will encode either a protein or protein fragment which at least substantially mimics the pharmacological properties of an HPV L1 or L2 protein, including the ability to form VLPs that are able to provoke an immune response against the HPV type of interest when administered to a human. Any such polynucleotide includes but is not necessarily limited to: nucleotide substitutions, deletions, additions, amino-terminal truncations and carboxy-terminal truncations.

In specific embodiments of the invention, the VLPs of at least one type of HPV include an HPV type selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82. However, any HPV type that is associated with a pathological condition or disorder is suitable for inclusion in the formulations provided herein. In some embodiments of the invention, the formulations are monovalent vaccine formulations which comprise VLPs of only one HPV type, e.g. HPV type 16, 18, 31, 45 or any of the HPV types listed above or any other HPV type associated with a pathological condition. In alternative embodiments, the formulations are bivalent; for example, formulations which comprise HPV VLPs of type 16 and 18. In alternative embodiments, the formulations are 3-valent, 4-valent, 5-valent, 6-valent, 7-valent, 8-valent, 9-valent or 10-valent. In some preferred embodiments, the formulation is 4-valent, for example, a formulation comprising VLPs of HPV types 6, 11, 16, and 18. In alternative preferred embodiments, the formulations comprise VLPs of HPV types 6, 11, 16, 18, 31, 33, 45, 52, and 58.

The amount of virus-like particles of each HPV type to be included in the formulations of the present invention is a therapeutically effective amount, which will depend on the immunogenicity of the expressed gene product. In general, an immunologically or prophylactically effective dose comprises about 10 µg to about 100 µg, and preferably about 20 µg to 80 µg of VLPs.

The concentration of HPV VLPs to be included in the formulations of the invention will vary; but generally a concentration of from about 20 µg/mL to about 200 µg/mL is preferred for each HPV VLP type present in the formulation. More preferably, the concentration of HPV VLPs, for each HPV type in the formulation, from about 40 µg/mL to about 160 µg/mL.

Aluminum Salt Adjuvants

As stated above, aluminum has long been shown to stimulate the immune response against co-administered antigens. The vaccine formulations of the invention are adsorbed to aluminum adjuvant. It is preferred that the aluminum adjuvant of the compositions provided herein is not in the form of an aluminum precipitate. Aluminum-precipitated vaccines may increase the immune response to a target antigen, but have been shown to be highly heterogeneous preparations and have had inconsistent results (see Lindblad E. B. *Immunology and Cell Biology* 82: 497-505 (2004)). Aluminum-adsorbed vaccines, in contrast, can be preformed in a standardized manner, which is an essential characteristic of vaccine preparations for administration into humans. Moreover, it is thought that physical adsorption of a desired antigen onto the aluminum adjuvant has an important role in adjuvant function, perhaps in part by allowing a slower clearing from the injection site or by allowing a more efficient uptake of antigen by antigen presenting cells.

The aluminum adjuvant of the present invention may be in the form of aluminum hydroxide ($Al(OH)_3$), aluminum phosphate ($AlPO_4$), aluminum hydroxyphosphate, amorphous aluminum hydroxyphosphate sulfate (AAHS) or so-called "alum" ($KAl(SO_4).12H_2O$) (see Klein et al., Analysis of aluminum hydroxyphosphate vaccine adjuvants by (27) Al MAS NMR., *J. Pharm. Sci.* 89(3): 311-21 (2000)). In exemplary embodiments of the invention provided herein, the aluminum adjuvant is aluminum hydroxyphosphate or AAHS. It is preferred that, in these embodiments, the aluminum adjuvant comprises phosphate and aluminum present in a molar ratio of about 0.1 to about 1.3 phosphate ($PO_4$) to aluminum (Al). In alternative preferred embodiments of this aspect of the invention, the phosphate to aluminum ratio is within the range of 0.1 to 0.70. It is more preferred that the aluminum adjuvant comprises phosphate and aluminum present in a molar ratio of about 0.2 to about 0.5 $PO_4/Al$. In alternative embodiments of this aspect of the invention, the aluminum adjuvant is aluminum hydroxide.

In some embodiments of the invention, the aluminum adjuvant is in the form of AAHS (referred to interchangeably herein as Merck aluminum adjuvant (MAA)). MAA carries zero charge at neutral pH, while $Al(OH)_3$ carries a net positive charge and $AlPO_4$ typically carries a net negative charge at neutral pH. MAA has a higher capacity to bind HPV VLPs than AlOH. In addition, VLPs adsorbed to MAA can induce a greater humoral immune response in mice than VLPs adsorbed to $Al(OH)_3$. Caulfield et al., *Human Vaccines* 3: 139-146 (2007). While not wishing to be bound by theory, it is possible that net charge of the aluminum adjuvant can affect its ability to bind the VLP antigen, with strongly charged adjuvants unable to bind antigen as strongly as neutral charged adjuvants. For this reason, it is preferred that the aluminum adjuvant of the pharmaceutical compositions of the present invention have zero point surface charge at neutral pH. One of skill in the art will be able to vary the buffer, salt concentration and/or percent of free phosphate in order to allow a zero point surface charge at neutral pH.

One of skill in the art will be able to determine an optimal dosage of aluminum adjuvant that is both safe and effective at increasing the immune response to the targeted HPV type(s). For a discussion of the safety profile of aluminum, as well as amounts of aluminum included in FDA-licensed vaccines, see Baylor et al., *Vaccine* 20: S18-S23 (2002). Generally, an effective and safe dose of aluminum adjuvant varies from 150 to 600 µg/dose (300 to 1200 µg/mL concentration). In specific embodiments of the formulations and compositions of the present invention, there is between 200 and 300 µg aluminum adjuvant per dose of vaccine. In alternative embodiments of the formulations and compositions of the present invention, there is between 300 and 500 µg aluminum adjuvant per dose of vaccine.

Methods of Making

In another aspect of the invention, a method for making a lyophilized HPV vaccine formulation that is resistant to stress induced by the lyophilization process is provided, wherein the HPV vaccine formulation is capable of retaining the physical and/or immunological characteristics of the liquid formulation. Thus, the invention provides a method of making a stable, lyophilized HPV vaccine formulation comprising: (a) formulating a liquid HPV vaccine formulation comprising (i) HPV VLPs of at least one HPV type adsorbed onto an aluminum salt adjuvant, wherein the VLPs of at least one HPV type are present in a concentration of 10-200 µg/ml and wherein the VLPs are selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; (ii) about 1% to about 10% w/v mannitol; and (iii) about 0.5% to about 10% sucrose; (b) freezing the liquid formulation to produce a frozen formulation and (c) drying the frozen formulation to provide a lyophilized HPV vaccine formulation. In preferred embodiments of this aspect of the invention, mannitol is present in a concentration ranging from about 4% to about 7% w/v and sucrose is present in a concentration of about 1% to about 5% w/v. Alternatively, any of the HPV vaccine formulations described herein may be used in the method described above.

In a further embodiment of this aspect of the invention, the liquid HPV vaccine formulation further comprises about 10 mM histidine, about 0.30M to about 0.35M NaCl and/or 0.01% PS80. In alternative embodiments, the method comprises (a) formulating a liquid HPV vaccine formulation as defined in any embodiment of the first aspect of the invention, (b) freezing the liquid formulation to produce a frozen HPV vaccine formulation and (c) drying the formulation to provide a lyophilized or freeze-dried vaccine formulation.

The process of lyophilizing (also known as "freeze-drying") formulations comprises two stages, namely (1)

freezing and (2) drying. The freezing step of the methods disclosed herein, which is the first step in the process of lyophilization, is carried out at temperatures below Tg' for an amorphous product or below Teu (eutectic temperature) for a product in a crystalline state for a length of time sufficient to allow for transformation of the liquid formulation into a solid state. The length of time required to transform the liquid formulation into a solid state depends in part of the total fill volume in the container used to lyophilize the formulation. When larger fill volumes are used, the length of time required to transform the liquid formulation into a solid state will be longer than when relatively smaller fill volumes are used for a comparable formulation.

At the end of the freezing step, the water present in the liquid formulation is converted into ice and typically less than 20% of water (w/w) is present as liquid. Additionally, the rate of cooling determines the size of ice crystals and the cake structure. Slow freezing, for example, usually results in formation of porous cake with larger ice crystals. One skilled in the art can readily determine the appropriate freezing temperature for carrying out the methods of the invention.

The second step of the freeze-drying process consists of drying. The drying step can be optimized based on the particular formulation, the shelf temperature, the container closure and the chamber pressure. It may be advantageous to incorporate additional steps into the lyophilization process, for example, a pre-freezing, step, an additional drying step or an annealing step may be added to the lyophilization cycle in order to make the freeze-dried HPV vaccine formulations of the invention. One skilled in the art can optimize the lyophilization cycle according to known procedures for a particular formulation of the invention (see, e.g. WO2011/017070).

In another embodiment of this aspect of the invention, the process comprises a further step wherein the vaccine formulation is reconstituted with a diluent to provide a reconstituted liquid formulation. Diluents useful for reconstituting the lyophilized formulations of the invention include any liquid that is a safe, stable, and pharmaceutically acceptable carrier. In some embodiments of the inventions, the formulations are reconstituted with SWFI and/or BWFI. SWFI containing a stabilizer, a solubilizer, a tonicity modifier, such as NaCl, $MgCl_2$, or $CaCl_2$ etc., and mixtures thereof are also useful in the methods described herein.

In another aspect of the invention, a method for making a frozen HPV vaccine formulation that is resistant to stress induced by freezing and thawing is provided, wherein the HPV vaccine formulation is capable of retaining the physical and/or immunological characteristics of the liquid formulation. Thus, the invention provides a method of making a stable, frozen HPV vaccine formulation comprising: (a) formulating a liquid HPV vaccine formulation comprising (i) HPV VLPs of at least one HPV type adsorbed onto an aluminum salt adjuvant, wherein the VLPs of at least one HPV type are present in a concentration of 10-200 μg/ml and wherein the VLPs are selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; (ii) about 1% to about 10% w/v mannitol; and (iii) about 0.5% to about 10% sucrose; and (b) freezing the liquid formulation to produce a frozen formulation. In preferred embodiments of this aspect of the invention, mannitol is present in a concentration ranging from about 4% to about 7% w/v and sucrose is present in a concentration of about 1% to about 5% w/v; in alternative preferred embodiments mannitol is present in a range of about 5% to about 6% w/v and sucrose is present in a concentration of about 2% to about 4% w/v. Alternatively, any of the HPV vaccine formulations described herein may be used in the method described above.

In a further embodiment of this aspect of the invention, the liquid HPV vaccine formulation further comprises about 10 mM histidine, about 50 mM to about 350 mM NaCl and/or 0.01% PS80. In alternative embodiments, the method comprises (a) formulating a liquid HPV vaccine formulation as defined in any embodiment of the first aspect of the invention, and (b) freezing the liquid formulation to produce a frozen HPV vaccine formulation.

Methods of Using

The present invention also provides a method of preventing or reducing the likelihood of infection of a human patient by an HPV comprising administration of a vaccine composition as disclosed herein.

In specific embodiments of the methods provided herein, the pharmaceutical composition that is administered to the patient comprises VLPs of HPV types 6, 11, 16, and 18. In additional embodiments, the compositions further comprise VLPs of HPV types 31, 33, 45, 52, and 58. In other embodiments, the compositions comprise HPV VLPs of HPV type 16 and further comprise VLPs of at least one additional HPV type selected from the group consisting of: HPV6, HPV11, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82.

Vaccine compositions of the present invention may be used alone at appropriate dosages which allow for optimal inhibition of HPV infection with minimal potential toxicity. In addition, co-administration or sequential administration of other agents may be desirable.

The formulations and compositions of the present invention may be administered to a patient by intramuscular injection, subcutaneous injection, intradermal introduction, or impression though the skin. Other modes of administration such as intraperitoneal, intravenous, or inhalation delivery are also contemplated. In preferred embodiments of the invention, the vaccines and pharmaceutical compositions are administered by intramuscular administration.

In some embodiments of this invention, the HPV pharmaceutical compositions and formulations disclosed herein are administered to a patient in various prime/boost combinations in order to induce an enhanced, durable, immune response. In this case, two pharmaceutical compositions are administered in a "prime and boost" regimen. For example the first composition is administered one or more times, then after a predetermined amount of time, for example, 2 weeks, 1 month, 2 months, six months, or other appropriate interval, a second composition is administered one or more times.

Preferably, the two or more HPV pharmaceutical compositions used in a clinical regimen comprise VLPs of the same HPV type or combination of HPV types. However, it may also be desirable to follow a clinical regimen in which two different HPV pharmaceutical compositions are administered to a patient with an appropriate interval of time separating the two vaccine administrations. For example, a vaccine composition comprising HPV 16 and 18 VLPs may be administered at one point in time, followed by an HPV vaccine composition comprising HPV 31, 33, 45, 52, and 58 VLPs at a second point in time, after a pre-determined length of time has passed. In such cases, each of the two different HPV vaccine compositions may be administered to the patient once, or more than one time, separated by an appropriate length of time.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

Example 1

Materials and Methods.
(a) Sample Preparation:
The Human Papillomavirus Quadrivalent (Types 6, 11, 16, 18) Vaccine, Recombinant, known as GARDASIL® (Merck and Co. Inc., Whitehouse Station, N.J.), was used as an exemplary vaccine in the studies described herein. GARDASIL® is a non-infectious recombinant, quadrivalent vaccine prepared from the highly purified virus-like particles (VLPs) of the major capsid (L1) protein of HPV types 6, 11, 16 and 18. GARDASIL® samples used in this study (referred to herein as "HPV 4-valent vaccine" or "HPV quadrivalent vaccine") consisted of final container lots manufactured as described previously (Lowe, R. S. et al., *J. Infect. Dis.* 176: 1141-45 (1997); Cook, J. C. et al., *Protein Expres Purif.* 17: 477-84 (1999). Briefly, type-specific HPV L1 proteins were produced by separate fermentations in recombinant *Sacharomyces cervisiae* and self assembled into VLPs. The VLPs were purified by a series of chemical and physical methods. Each of the purified aqueous VLPs were adsorbed on preformed Merck's aluminum hydroxyphosphate sulfate adjuvant (MAA) individually. The monovalent vaccine components were formulated in 10 mM histidine, 0.01% Polysorbate 80, and 0.33 M sodium chloride. The four individual monovalent (adjuvant adsorbed) vaccines were blended at protein concentrations of 40, 80, 80 and 40 µg/ml for HPV types 6, 11, 16, and 18 respectively, to form the quadrivalent dosage form of GARDASIL®.

For long-term stability studies, HPV samples were prepared as described above. Additionally, samples were prepared which comprised 1×MAA without antigen. To prepare 2×MAA samples, buffered salt solution (6.1 mM sodium phosphate and 120 mM sodium chloride) aid 5.44% aluminum potassium sulfate solution were combined in a tank. 1.0 N sodium hydroxide was added to the tank to precipitate the adjuvant and to bring the pH to a target of 7.7-7.8 at 2-8° C. The pH-adjusted solution was concentrated 3-fold by recirculation through 200,000 nominal molecular weight cutoff (MWCO) filters aid then diafiltered against a target of 2.1 volumes of physiological salt solution (0.9% sodium chloride) to reduce the content of potassium and sulfate ions. Following the diafiltration, the adjuvant was diluted to a target aluminum concentration of 900 µg/mL (2×MAA) with physiological salt solution aid 1.4% sodium borate solution. The 2×MAA was further diluted 1:1 with physiological salt solution (0.9% sodium chloride) to prepare the 1×MAA used in this study.

(b) Composition of Buffers.
HPV vaccine formulations containing the quadrivalent HPV types bound to MAA were buffer exchanged with 18 buffers using a settle/decant process. All the buffers had the base formulation of 10 mM histidine, 0.01% Polysorbate 80, pH 6.2 with different compositions of excipients, as shown in FIG. 1.

A brief description of the buffers used in this study, along with identifying buffer numbers ("Buffer code") is shown below (Table 1):

TABLE 1

Buffer Compositions

| Buffer | Excipients | Buffer Code Sodium Chloride (mM) | | |
|---|---|---|---|---|
| | | 0 | 150 | 320 |
| Buffer-A | 5% Mannitol | B-1 | B-7 | B-13 |
| Buffer-B | — | B-2 | B-8 | B-14 |
| Buffer-C | 5% Mannitol, 2% Sucrose | B-3 | B-9 | B-15 |
| Buffer-D | 6% Mannitol, 4% Sucrose | B-4 | B-10 | B-16 |
| Buffer-E | 8% Sucrose | B-5 | B-11 | B-17 |
| Buffer-F | 2% Glycine, 1% Sucrose | B-6 | B-12 | B-18 |

For long-term stability studies, HPV vaccine formulations containing the quadrivalent HPV types bound to MAA and 1×MAA adjuvant alone were buffer exchanged with 5 of the above buffers. (Buffer-B through Buffer-D with 0 or 320 mM NaCl (i.e., buffers B-14, B-3, B-15, B-4, and B-16). Buffer B-2 was not tested in long term stability studies).

(c) Freeze Thaw Study:
HPV vaccine formulations comprising buffers B-1 through B-18 (see Table 1) were subjected to either fast flash freezing (FF) using liquid nitrogen blast at −115° C. for 15 minutes or normal freezing at −70° C. for 1 hour. The flash freezing was cycled at 1× (1×FF) and the normal freezing was cycled at 1× and 3×. The test formulations were filled in 3 mL glass vials with a fill volume of 0.6 ml. Frozen vaccine samples were thawed at ambient temperature for 1 hour. Following the freeze thaw cycles, the potency of the samples was analyzed and other characterization assays were performed.

For long-term stability studies, the HPV vaccine formulations and 1×MAA formulations described above were subjected to normal freezing at −70° C. and the frozen formulations were stored at −70° C. for approximately 24 hours. The test formulations were filled in 3 mL glass vials with a fill volume of 0.6 ml. Frozen vaccine samples were thawed at ambient temperature for 1 hour. Following the freeze thaw cycle, the vials were held at 2-8° C. for 1 month before subjecting them to long term stability studies. The potency of the samples was analyzed and other characterization assays were performed at several time points for both HPV formulations and 1×MAA formulations.

(d) Lyophilization Study:
HPV formulations comprising buffers B-1 through B-18 (see Table 1) were subjected to lyophilization with freezing done either by fast flash freezing (FF) using liquid nitrogen blast at −115° C. for 15 minutes or using a pre-cooled lyophilization shelf. The vaccine samples were kept in 3 mL glass vials with a fill volume of 0.6 mL. Frozen vaccine samples were lyophilized using standard lyophilization process parameters. Briefly, the samples were loaded on a pre-cooled shelf at −50° C. in the lyophilizer and the shelf was held at −50° C. for 1 hour. An annealing step was then carried out at −20° C. (ramped at a rate of 0.5° C./min) for 2 hours. The shelf was then cooled back to −50° C. (ramped at a rate of 0.5° C./min) and held for 2.5 hours. Primary drying was conducted by heating the shelf to −20° C. at 1° C. per minute under a pressure of 100 mTorr for 48 hours. Secondary drying was performed at a temperature of 10° C. for 4 hours at 0.5° C./min. Post lyophilization, the vials were backfilled with nitrogen gas, stoppered under partial vacuum and unloaded. The freeze dried vaccine samples were stored frozen for further analysis.

For long-term stability studies, HPV vaccine formulations and 1×MAA formulations were subjected to lyophilization with freezing done using a pre-cooled lyophilization shelf. Vaccine samples were filled as described above. Frozen vaccine samples were lyophilized using standard lyophilization process parameters as described above. Freeze dried vaccine vials were stored frozen until subjected to long term stability studies.

(e) Accelerated Stability Study:

Stability studies were carried out under accelerated temperature conditions for all the 4-valent HPV vaccine formulations comprising buffers B-1 through B-18 (see Table 1). Lyophilized 4-valent HPV test samples in various formulation buffers along with the respective non-lyophilized liquid 4-valent HPV formulations were placed in accelerated temperature conditions at 45° C. for 1 month. This temperature was chosen because the inactivation rate of HPV VLPs is very sensitive to temperature. The samples were stored in certified stability chambers. At the end of the stability study, samples were analyzed for their physical appearance, and then evaluated for potency and other characterization studies after reconstitution.

(f) In Vitro Antigenicity Assays.

To release HPV from the aluminum adjuvant, an aluminum dissolution method was developed which included dilution of the HPV-aluminum formulations into a high salt solution containing citrate and Polysorbate 80. Following the aluminum dissolution method, the HPV VLP samples were directly subjected to an in vitro antigenicity assay using a surface plasmon resonance instrument.

The in vitro antigenicity of the HPV VLPs was determined by measuring the affinity of the VLPs for HPV-specific neutralization antibodies using a surface plasmon resonance technique on a Biacore® 2000 or 3000 instrument (GE Healthcare Biosciences AB, Piscataway, N.J.). The anti-HPV antibody was immobilized by binding to rat-mouse antibody $Fc_\gamma$ chemically coupled to the surface of a Biacore sensor chip CMS. The interaction of HPV VLP antigen in the flow phase with the antibody on the surface of the sensor chip was recorded based on sensor chip reflection index change induced by the binding of the antibody to the antigen. The HPV VLP samples from the aluminum adjuvanted formulation studies were directly compared to a freshly thawed frozen stock solution of the same HPV VLP (reference standard) to determine in vitro antigenicity.

(g) Dynamic Light Scattering (DLS).

Particle size measurements were made at ambient temperature using a DynaPro® dynamic light scattering instrument (Wyatt Technology Corp., Santa Barbara, Calif.). The instrument was calibrated using polymer latex size standards. HPV VLP samples obtained using the aluminum dissolution method described above were directly subjected to DLS measurements. The cumulant analysis of the auto-correlation function for scattered intensity variations due to Brownian motion of VLPs in solution yielded average diffusion coefficients (Koppel, D. E. *J. Chem. Phys.* 37: 4814-20 (1972)). The Z-average hydrodynamic diameter value was obtained based on average diffusion coefficients by using the Stokes-Einstein equation. The apparent hydrodynamic size of antigen particles was recorded as Z-average hydrodynamic diameter ($D_h$). All data reported here are the averages of five measurements of the same sample.

(h) Static Light Scattering (SLS).

Particle size measurements were made at ambient temperature using a Malvern® Mastersizer 2000 static light scattering instrument (Malvern Instruments; Worcestershire, United Kingdom). Laser diffraction technique is used to measure the size of the particles. The instrument was calibrated using polymer latex size standards. 1×MAA samples were diluted in water and then subjected to SLS measurements. Particle size (0.5) in microns (μm), retrieved through the mean intensity distribution as a factor of scattering direction, was plotted as a function of various test conditions (F/T FF 1× and LYO along with the respective control).

(i) Osmolality Measurements.

An Advanced® Model 3300 Micro-Osmometer (Advanced Instruments Inc., Norwood, Mass.) was used for this study. This instrument uses 20 μl of sample to measure sample osmolality by freezing point depression. Supercooling of the sample was initiated by the insertion of a specially designed, disposable holder containing the sample into the instrument's thermistor probe, which was in a fixed position. Following a solenoid-induced pulse and subsequent sample freezing, the liberated heat of fusion was related by a microprocessor to the sample's freezing point and osmolality was shown on a digital display. Calibration of the instrument was performed by running 2-5 samples at each of two calibration levels (50 and 850 mOsm/kg). Internal calibration was automatically performed by the instrument after an acceptable repeatability was established. Following the calibration of the instrument, the reference standard Clinitrol™ 290 (290 mOsm/kg), supplied by Advanced Instruments, was measured. Test samples of HPV formulations were measured following the reference standard.

(j) Dry Cake Physical Appearance:

Promoting desired pharmaceutical elegance during product development efforts generally includes establishing the range of acceptable product appearance standards. Evaluating attributes of the dried cake entails a description of the physical attributes such as color, density, uniformity, and evidence of shrinkage, collapse, or meltback. The appearance of the lyophilized HPV vaccine formulations was evaluated subjectively based on the quality attributes as specified below (Table 2).

TABLE 2

| Quality | Appearance |
|---|---|
| ++++ | Elegant Cake |
| +++ | Slightly Collapsed Cake |
| ++ | Cake with cracks and Shrunk |
| + | Completely Collapsed Cake |

(k) Reconstitution Time.

Reconstitution rate is a product characteristic dependent on the formulation. The reconstitution time of the dried HPV vaccine formulations was determined by monitoring the time for complete dissolution of the freeze dried cake upon addition of sterile water for injection, as indicated by the presence of a homogeneous suspension. About 0.5 to 0.6 ml of sterile WFI was added to each of the lyophilized HPV vaccine formulation based on the formulation excipient levels. In order to maintain the desired concentrations of the HPV VLPs, the final volume of the formulations after reconstitution was kept close to 0.6 ml.

(l) Shake Test.

A shake test was performed on the alum-adsorbed vaccines to determine if the vaccine formulations were frozen during cold chain excursions. Freezing of the vaccine formulations irreversibly alters the structure of the alum and markedly reduces vaccine immunogenicity. Freezing of an alum-based vaccine leads to breaking of the lattice structure, resulting in agglomeration of the alum content and faster sedimentation. A faster rate of sedimentation forms the basis of a positive shake test, which attempts to compare the rate of sedimentation in the test and control vials. Vaccine potency is confirmed if the test vial, known to be previously frozen or freeze dried, shows a similar sedimentation rate as that of a control vial which was not previously frozen or freeze dried. If a faster sedimentation rate is observed for the test vial relative to the control vial, the vaccine is considered unsafe for use due to the presence of agglomerated alum.

In order to measure the sedimentation rate, the test vials and the control vials were mixed to obtain a homogeneous suspension of the vaccine formulations. After mixing, the vials were set aside and the time for sedimentation was measured. If the vaccine was not uniformly mixed or if sediments/flocculation was still found settled at the bottom at a faster rate, one could conclude that the test vial was frozen/freeze dried that could have damaged the alum structure to form big agglomerated alum particles. All HPV vaccine formulations that were either freeze-thawed or lyophilized and reconstituted were analyzed by shake test to assess their quality.

Example 2

In Vitro Antigenicity

In-vitro antigenicity of 4-valent HPV vaccine formulations comprising HPV VLPs was evaluated using a neutralization antibody binding assay (Surface Plasmon Resonance, Biacore). The analysis for antigen bioactivity was determined using the Biacore 2000 and Biacore 3000 instruments (GE Healthcare Biosciences AB, Piscataway, N.J.). Biacore was performed for the 4-valent HPV vaccine test formulations that were either freeze-thawed or lyophilized. The lyophilized 4-valent HPV formulations were reconstituted with sterile water for injection as described in EXAMPLE 1 prior to aluminum dissolution. All test formulations comprised HPV type 6, 11, 16, and 18 VLPs suspended in buffers B-1 through B-18 diluted with dissolution buffer.

All 4 types of HPV VLP antigens in each 4-valent HPV vaccine formulation were assayed for in vitro antigenicity by Biacore analysis. The Biacore conditions utilized were as described in Mach et al. (*J. Pharm. Sci.* 95: 2195-2206 (2006)), with modifications. All samples were treated with the aluminum dissolution method described in EXAMPLE 1 to release the HPV VLP antigens from the aluminum adjuvant prior to analysis in the Biacore assay. The HPV VLPs sample from the aluminum adjuvanted studies are directly compared to a frozen stock solution of the same HPV VLP to determine in vitro antigenicity. The freshly thawed frozen stock solution of the HPV VLP served as the Biacore assay reference. The aluminum-dissolved HPV samples were either used directly or further diluted to match the concentrations of frozen stock solution references for each HPV type before Biacore measurement. The Biacore data of the test HPV formulations, both freeze thawed and lyophilized formulations from all the buffers (B-1 to B-18) were normalized with control HPV formulations in same buffers (B-1 to B-18), that was neither freeze thawed nor lyophilized. The reported Biacore values were the average of two measurements per sample formulation.

Normalized Biacore data for each HPV type in each of the HPV test formulations following 1× freeze-thaw, 3× freeze-thaw, and 1× flash freezing is shown in FIG. 2. All 4-valent HPV vaccine formulations that underwent the freeze thaw process were fully potent, and possessed almost identical Biacore responses as the reference standards for all the four HPV types tested, except for formulation buffer B-2 (Buffer B+0 mM NaCl), which did not have any salt or excipients. The impact on the antigenicity for all the HPV types was more pronounced for Buffer B in the absence of salt and excipients (B-2) when 3× freeze-thaw was performed. There was no significant difference in antigenicity for all the HPV types amongst the 1× normal freeze-thaw samples and the 1× flash freeze thaw samples. It can be concluded from the data that the presence of salt, excipients or both are needed to retain the antigenicity of the HPV types in order to withstand the stress associated with freeze-thawing.

Normalized Biacore data for each HPV type in each of the various HPV vaccine formulations following lyophilization using a pre-cooled shelf or flash freezing during the lyophilization process (see Example 1) is provided in FIG. 3. The Biacore results indicated that the antigenicity for all the HPV types dropped for Buffer-B (B-2, B-8 and B-14) that did not have any excipients, while the antigenicity for the rest of the formulation buffers was identical to the reference standards. There was no significant difference in antigenicity for all the HPV types amongst the pre-cooled freezing samples and flash-freezing samples during lyophilization. The HPV vaccine formulation in Buffer B-2 and its corresponding salt buffers (B-8 and B-14) were not able to sustain the lyophilization process. A drop in antigenicity was observed for all the HPV types in formulation Buffer B (B-2, B-8 and B-14). The antigenicity drop was significantly higher in the absence of salt (B-2) and it improved with increase in salt concentration. For buffers that contained 5% mannitol and salt (Buffer A+150 mM NaCl (B-7) and Buffer A+320 mM NaCl (B-13)), a drop in antigenicity by 10-15% was observed for all the HPV types. As seen from the FIG. 3, all buffers that did not have combination of excipients in their formulation were not able to withstand the stress associated with the lyophilization process. Formulation buffers C and D that comprised of combination of excipients, mannitol and sucrose, were able to maintain the integrity of the HPV VLPs and hence retained vaccine antigenicity even after the lyophilization process. This suggests a role of these excipients in combination as a vaccine stabilizer compared to Buffer-E (sucrose only) or Buffer-A (mannitol only) formulations.

Lyophilized 4-valent HPV vaccine formulations (B-1 to B-18) used in the above-described lyophilization studies were stored in lyophilized solid form at 45° C. for 1 month in order to evaluate the storage stability of the lyophilized vaccines. Non-lyophilized liquid 4-valent HPV vaccine formulations (B-1 to B-18) were used as the respective controls in evaluating the storage stability of the lyophilized HPV vaccine formulations. After storage at 1 month at 45° C., the lyophilized formulations were evaluated for physical appearance and then reconstituted as described in Example 1 with sterile water for injection. The test samples were evaluated for antigenicity using Biacore as described in Example 1. Normalized Biacore data for each HPV type in each of the various HPV vaccine formulations after 1 month storage at 45° C. is provided in FIG. 4. The antigenicity for all the HPV types in the non-lyophilized liquid 4-valent HPV formulations in various buffers was around 20-40% after 1 month storage at 45° C., indicating the HPV VLP antigens were not stable in the liquid formulations under the given storage conditions. On the other hand, lyophilized HPV formulations in Buffer-C (B-3, B-9, B-15) in both types of lyophilized process (Lyo PC and Lyo FF) that were stored at 45° C. for one month exhibited significantly higher antigenicity values than their non-lyophilized liquid counter parts. The lyophilized HPV formulations that contained sucrose alone in their formulation, Buffer-E (B-5, B-11 and B-17) were colored after 1 month storage at 45° C. due to the instability of sucrose (degradation). It was believed that the degraded sucrose samples were inhibiting the binding of the HPV antibody on to the immobilized chip causing instrument failures and hence some of the data points were missing in FIG. 4. Results indicate that Buffer C (B-3) and its corresponding salt containing buffers (B-9 and B-15) were able to retain the antigenicity of the HPV VLPs to 80-90% for most of the HPV types even after 1 month storage at 45° C. A drop in antigenicity was observed for Buffer D with no salt (B-4), while its corresponding salt containing buffers (B-10 and B-16) retained the antigenicity for most of the HPV types even after 1 month storage at 45° C. Thus, based on the stability profile, it can be concluded that buffers that contained mannitol and sucrose combinations provided a stable vaccine product with desired antigenicity.

Example 3

Osmolality Measurements.

Figure 5:
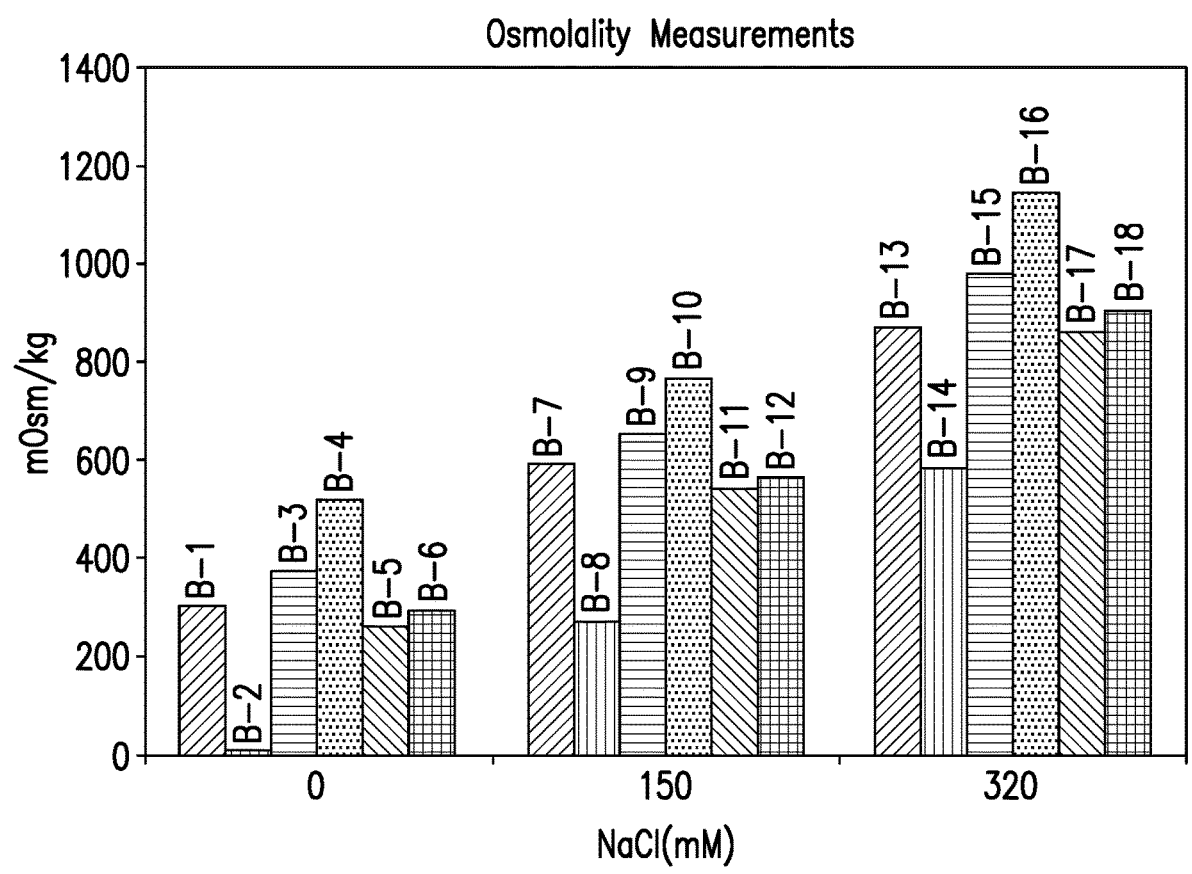
FIG. 5 provides a plot of osmolality measurements (mOsm/kg) for HPV 4-valent test formulations in Buffer A through Buffer F with 0, 150, or 320 mM sodium chloride. See Example 3.

Osmolality measurements were performed on all the control 4-valent HPV formulations in various buffers (B-1 through B-18) prior to either freeze thaw or lyophilization process. Results indicate that there is an increase in osmolality values with increase in salt concentration for all the buffers (FIG. 5). The contribution to the osmolality is mainly from the excipients (mannitol, sucrose, and glycine) and salt (sodium chloride) and not from the histidine, HPV antigens or MAA (as seen in the case of buffer B-2, which has the least osmolality). The osmolality for HPV 4-valent vaccine that was in formulation buffer B-14 (similar to the current Gardasil® formulation) was around 585 mOsm (FIG. 5). Buffers B-13 through B-18 (see Table 1), with the exception of buffer B-14 had excipients with high salt concentration that contributed to the higher tonicity for those formulations. In contrast, buffers B-1 through B-12, with the exception of buffers B-9 and B-10, had excipients with low salt concentration that contributed to low tonicity values. The combination of salt and excipients play a major role in defining the tonicity of the given HPV 4-valent vaccine formulation.

Example 4

Particle Size Measurements.

Particle size measurements were performed on all the 4-valent HPV vaccine formulations that included the freeze-thawed formulations (after 1×, 3× normal freeze-thaw cycle and 1× flash freeze-thaw cycle, as described in Example 1(c)) and lyophilized formulations (after lyophilization with flash freezing or lyophilization with a pre-cooled lyophilization shelf, as described in Example 1 (d)) from all the buffers (Buffer-A through Buffer-F) as well as control 4-valent HPV vaccine formulations in the same buffers (Buffer-A through Buffer-F) that were neither freeze thawed nor lyophilized. All samples were treated with the aluminum dissolution method described in Example 1(f) to release the HPV VLP antigens from the aluminum adjuvant prior to particle size measurements. The particle size distribution is the average measure of the size distribution of all the HPV VLPs present in the solution after aluminum dissolution. The z-average values that correspond to the particle size distribution for all the 4-valent HPV formulations in various buffer compositions are shown in FIG. 6.

Figure 6:
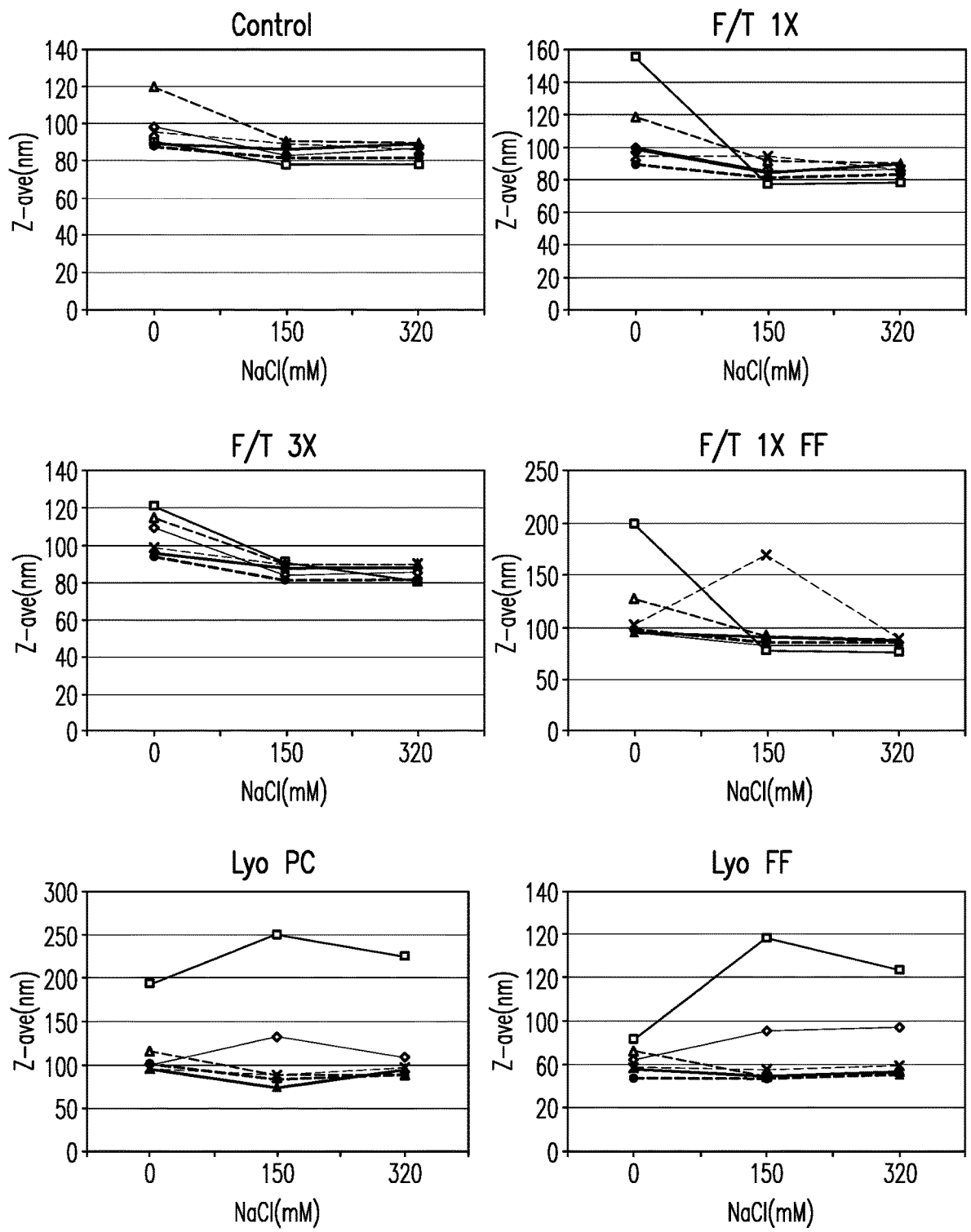
FIG. 6 shows plots of particle size measurements (Z-ave, nm) for each of the HPV 4-valent test formulations in various buffers as a function of sodium chloride concentration after freeze thaw and lyophilization conditions. For all plots, results depicted represent Buffer-A (white diamond), Buffer-B (white square), Buffer-C (black triangle), Buffer-D (black x), Buffer-E (white triangle) and Buffer-F (black circle). Shown are results for test formulations following freeze-thaw ("F/T 1×"), freeze-thaw 3× ("F/T 3×"), flash freezing ("F/T 1×FF"), lyophilization with freezing done by flash freezing ("Lyo FF") and lyophilization using a pre-cooled lyophilization shelf ("Lyo PC"). Results are also provided for control formulations that were not subjected to either freeze-thaw or lyophilization. See Example 4.

As seen in FIG. 6, the particle size was slightly larger for control and freeze-thawed (1×, 3× and 1×FF) 4-valent HPV formulations in all the buffers that contained no salt (Buffer-A through Buffer-F with 0 mM sodium chloride) than those buffers containing salt (Buffer-A through Buffer-F with 150 or 320 mM sodium chloride), with the exception of Buffer-D with 150 mM sodium chloride (B-10, see FIG. 1), which showed the greatest particle size measurements. In the presence of salt, all the 4-valent HPV formulations including the control 4-valent HPV formulations had the particle size distribution within the 80 to 100 nm range that is typically expected for HPV VLPs present in the dissolution buffer. Among the different test formulations evaluated, those with Buffer-C and Buffer-D, which comprise a combination of excipients (mannitol and sucrose), were impacted less by the stress of the freeze thaw conditions, as far as the particle size distribution of the VLPs compared to those formulations that did not comprise a combination of excipients mannitol and sucrose.

In case of lyophilized 4-valent HPV vaccine formulations, the particle size distributions for the HPV VLPs were larger for buffers that contained either no excipients or just mannitol as excipient in their formulation composition (Buffer-A and Buffer-B, see FIG. 6) as compared to the other 4-valent HPV vaccine formulations (Buffer-C to Buffer-F) that were lyophilized and also when compared to their respective non-lyophilized control 4-valent HPV vaccine formulations. The particle size increase was significant for lyophilized 4-valent HPV vaccine formulations in Buffer-A and Buffer-B in the presence of sodium chloride. The particle size distributions for the HPV VLPs in the lyophilized formulations comprising Buffer-C, Buffer-D and Buffer-F were within the normal range of 80-100 nm irrespective of salt concentration and were comparable to the respective non-lyophilized control 4-valent HPV formulations. The lyophilized 4-valent HPV formulation that had only sucrose as its excipient (Buffer-E) had larger particle size distribution for the HPV VLPs in the absence of sodium chloride (Buffer-E with 0 mM sodium chloride) and normal particle size distribution within the range of 80-100 nm for the HPV VLPs in the presence of sodium chloride (Buffer-E with 150 or 320 mM sodium chloride).

Overall, the 4-valent HPV vaccine formulations in Buffer-A, Buffer-B, Buffer-D and Buffer-E that contained no sodium chloride in their buffer composition were not able to sustain the freeze thaw and lyophilization process stress, even when these buffers had surfactant in their buffer composition. Surfactants typically are known to prevent the aggregation of proteins that are undergoing freeze thaw and lyophilization process stress (Bhambhani et al., *Am. Pharm. Rev.* 13(1): 31-38 (2010); Chang et al., *J. Pharm. Sci.* 12: 1325-30 (1996)). On the other hand, 4-valent HPV vaccine formulations that were in Buffer-C and Buffer-D, which contained combination of excipients in their buffer composition either with or without sodium chloride, were quite stable to the freeze thaw and lyophilization process stress conditions. The presence of this combination of excipients (mannitol and sucrose) in these buffers either with or without sodium chloride was able to preserve the integrity of the HPV VLPs that are bound to the MAA during the freeze thaw and lyophilization process conditions.

Example 5

Characteristics of Lyophilized 4-Valent HPV Formulations (a) Dry Cake Physical Appearance.

The physical appearances of all the lyophilized cakes were photographed right after lyophilization (T=0) and after 1 month storage at 45° C. The appearance of the cakes was visualized by two analysts and based on the morphology, color, and other quality attributes, the cakes were categorized as described in Example 1 (see Table 2). In general, dry white solid cakes were obtained for all the 4-valent HPV formulations. FIG. 7 describes the physical appearance of all lyophilized HPV formulations in various buffers based on 3 vials per each formulation. Elegant cakes were observed for buffers B-1, B-3, B-4, B-6, and B-13 and slightly collapsed or cracked or shrunk cakes for buffers B-7, B-8, B-9, B-10, B-14, B-15 and B-16. Completely collapsed cakes were observed for buffers B-5, B-11, B-12, B-17 and B-18 following lyophilization either using flash freezing or a pre-cooled shelf. In addition, a completely collapsed cake was observed for the formulation in buffer B-2 following lyophilization using flash freezing. Results from this study indicate that the physical appearance of the cake was dependent on the formulation excipients. In formulations that contained sucrose alone (B-5, B-11 and B-17), or sucrose in combination with glycine and salt (B-12 and B-18), the cakes were completely collapsed following lyophilization either using flash freezing or a pre-cooled shelf. Unlike the formulations comprising sucrose alone, elegant cakes were observed for formulations comprising mannitol alone or sucrose in combination with mannitol or glycine without the presence of salt. The quality of the cakes for formulations that contained the combination excipients of mannitol and sucrose decreased with increase in salt concentration.

The physical appearance of all lyophilized HPV formulations in various buffers were also recorded following the storage at 45° C. for 1 month. Results indicate that the morphology or the physical appearance of the lyophilized cakes did not change after 1 month storage at 45° C., except for formulations in buffers B-5, B-11 and B-17 (Buffer-E) that turned yellow to brown in color due to the instability of sucrose at elevated temperature. There was no color change observed for formulations that comprised combination of sucrose and mannitol or glycine. FIG. 7 describes the physical appearance of all lyophilized HPV formulations in various buffers that were stored for 1 month at 45° C.

(b) Reconstitution Time.

The lyophilized 4-valent HPV vaccine formulations were reconstituted with sterile water for injection (WFI) based on the amount of the excipients present. The volume of WFI that was added to each formulation ranged from 0.50 and 0.60 ml. The final volume after reconstitution was approximately 0.6 ml. The reconstitution time was monitored using a stop watch and the time for complete dissolution (in this case homogeneous suspension) was recorded for each of the HPV vaccine formulations following lyophilization. The reconstitution times are shown in FIG. 8 for samples that were reconstituted right after lyophilization and for samples that were stored at 45° C. for 1 month.

Most of the formulations had a fast reconstitution time of less than 15 seconds, while the formulation buffer that contained sucrose alone, Buffer-E (B-5, B-11 and B-17) had a slower reconstitution time of 90 seconds or higher. The same trend was observed for samples that were stored at 45° C. for 1 month. The formulations in Buffer-E (B-5, B-11 and B-17) that contained sucrose alone were yellow to brown color when stored at 45° C. for one month. Upon reconstitution of these samples, the yellow to brown color of the formulation was still retained due to the degradation of sucrose during storage at high temperature for one month.

(c) Shake Test.

After reconstitution of all the lyophilized 4-valent HPV vaccine formulations, a shake test was performed to check the quality of the vaccine formulation. The time for the alum particles to settle down at the bottom of the vial was measured for each of the test formulations. The shake test time for all the 4-valent HPV formulations are shown in FIG. 9. The formulation buffer that contained no excipients, but salt (Buffer-B with either 150 or 320 mM sodium chloride) had a faster settling time indicating the alum particles were agglomerated. In all other formulations, the settling time was greater than 10-15 minutes, indicating that the alum particles were not agglomerated. The presence of excipients in the 4-valent HPV vaccine formulation prevents the agglomeration of alum particles even after freeze thaw and lyophilization stress.

Long-Term Stability Studies (Examples 6-9)

Long term stability studies were carried out under various storage temperature conditions for the HPV and 1×MAA test formulations. Freeze-thawed and lyophilized 4-valent HPV test samples and 1×MAA test samples in various formulation buffers were placed at various storage temperature conditions (−70° C., 2-8° C., 25° C. and 37° C.) for over 6 months with sampling time points at T=0, T=1 month, T=3 months and T=6 months (see Table 3 for study design). At the end of each stability time point, the potency and physical appearance of the samples was analyzed and other characterization studies were performed.

For the 6-month time point, samples were stored at the specified time for 198 days (>6 months) to allow determination of the Vaccine Vial Monitor (VVM) category, which is based on heat stability. The VVM system, implemented by the World Health Organization (WHO), utilizes chemical time-temperature indicator labels on vaccine vials as a way of detecting cumulative exposure of a vaccine to heat over time. The labels allow health care workers to determine if a vaccine has been exposed to temperatures at which it is no longer potent based on a color change of the VVM and, thus should be discarded. The rate at which the label changes color is modified based on its VVM category so that the VVM color change rate approximates the time and temperature sensitivity of a vaccine.

VVM categories, as defined by WHO, are as follows: VVM30 (high stability)—stable for 193 days at 25° C., stable for 30 days at 37° C.; VVM14 (medium stability)—stable for 90 days at 25° C., stable for 14 days at 37° C.; VVM7 (moderate stability)—stable for 45 days at 25° C., stable for 7 days at 37° C.; VVM2 (low stability)—stable for 2 days at 37° C.

TABLE 3

| | Storage Temperature | | | |
|---|---|---|---|---|
| Storage Time | −70° C. | 2-8° C. | 25° C. | 37° C. |
| T = 0 | — | ✓ | — | — |
| T = 1 M | — | ✓ | ✓ | ✓ |

TABLE 3-continued

| | Storage Temperature | | | |
|---|---|---|---|---|
| Storage Time | −70° C. | 2-8° C. | 25° C. | 37° C. |
| T = 3 M | — | ✓ | ✓ | ✓ |
| T = 6 M | ✓ | ✓ | ✓ | — |

Example 6

In Vitro Antigenicity

In-vitro antigenicity of 4-valent HPV vaccine test formulations was evaluated using a neutralization antibody binding assay (Surface Plasmon Resonance, Biacore). Freeze-thawed and lyophilized 4-valent HPV test samples were stored at −70° C., 2-8° C., 25° C. and 37° C., as described in Example 1, for a period of over 6 months in order to evaluate the storage stability of the HPV vaccine formulations in various buffers. Antigen bioactivity analyses were performed at each time point of the long term stability study. Preparation of samples for Biacore analysis was as described in Example 2. All test formulations comprised HPV type 6, 11, 16, and 18 VLPs suspended in Buffer-B through Buffer-D diluted with dissolution buffer. The Biacore data of the test HPV formulations were normalized with control HPV formulations in same buffers that were neither freeze-thawed nor lyophilized. Reported Biacore values were the average of two measurements per sample formulation.

Figure 10A:
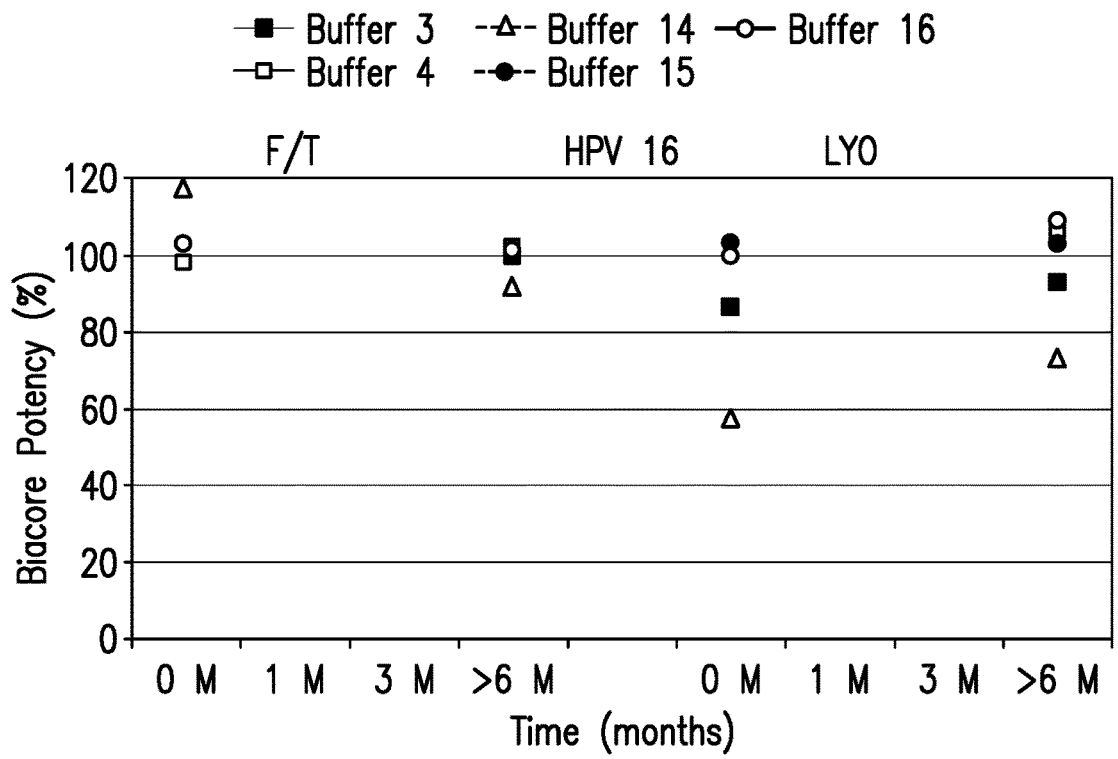
FIGS. 10A and 10B provide the in vitro antigenicity for HPV types 16 (FIG. 10A) and 18 (FIG. 10B) in the 4-valent test formulations (Buffer-B through Buffer-D) following storage for various time points at −70° C. Test formulations were stored after being subjected to freeze-thaw (F/T) or lyophilization processes (LYO), as described in Example 1. Shown is the Biacore potency (%) as a function of storage time. See Examples 1 and 6.
Figure 10B:
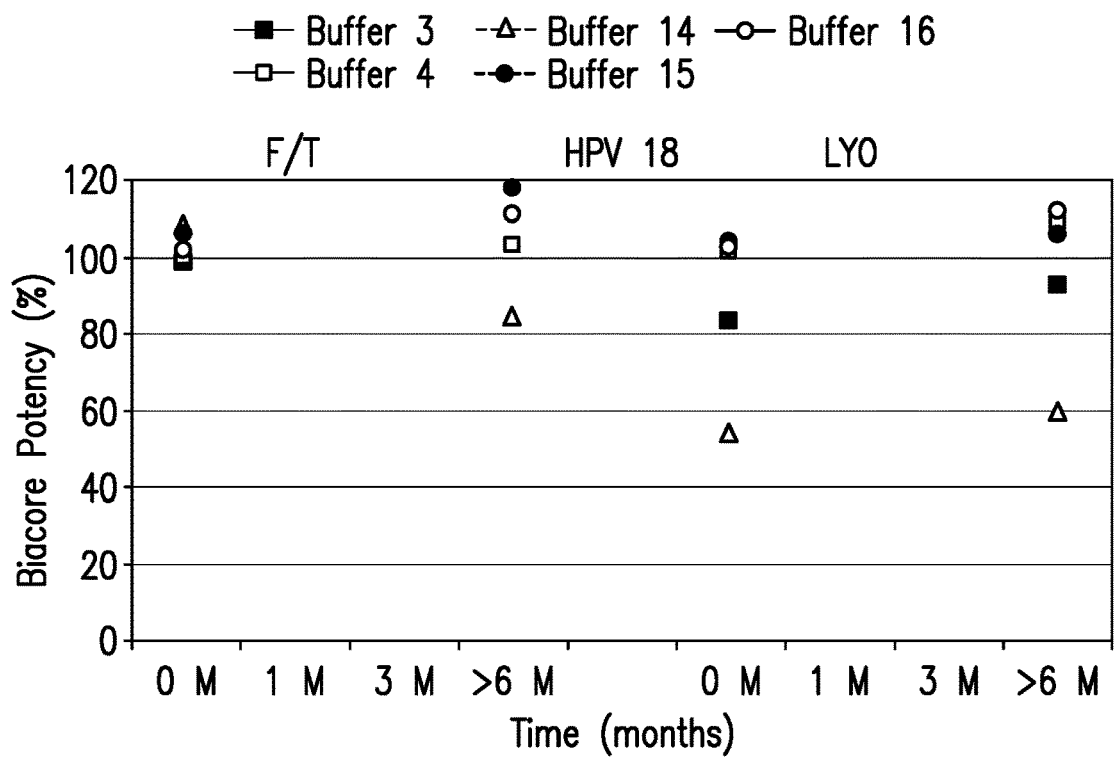

Normalized Biacore data indicate that HPV vaccine formulations in Buffer C and Buffer D that underwent the freeze-thaw process followed by storage at −70° C. for over 6 months were fully potent, and possessed almost identical Biacore responses as the reference standards for all four HPV types tested (see FIG. 10 for representative data for HPV types 16 and 18). HPV vaccine formulation in Buffer B (Buffer-14) showed a slight loss of potency at the 6 month time point for all four HPV types. It can be concluded from the data that the presence of salt, excipients and/or both are needed to retain the antigenicity of the HPV types in order to withstand the stress associated with freeze-thaw and storage.

The Biacore results of the lyophilized HPV formulations that were stored at −70° C. for over 6 months indicated that the antigenicity for all HPV types dropped for Buffer-B (Buffer-14) at all time points including the T=0 time point as compared to HPV formulations in Buffer-C and Buffer-D (see FIG. 10 for representative date for HPV types 16 and 18). This can be viewed as an amplification of the potency drop observed under freeze thaw conditions in Buffer-14 formulation after 6 months storage at −70° C. Because Buffer-14 comprises only salt (i.e., no excipients), it could not sustain the freeze drying process (drop in potency at T=0 time point). The antigenicity for all HPV types in test formulations comprising sucrose and mannitol (Buffer-C and Buffer-D) was identical to the reference standards, indicating that these buffers were able to maintain the integrity of the HPV VLPs and hence retained vaccine antigenicity when stored at −70° C. for over 6 months following the lyophilization process. This strongly elucidates the role of these excipients in combination as a vaccine stabilizer under the given test conditions.

All 4-valent HPV vaccine formulations (Buffer-B through Buffer-D) that underwent the freeze-thaw process, except the formulation comprising Buffer-14, were fully potent, and possessed almost identical Biacore responses as the reference standards for all four HPV types tested following storage at 2-8° C. for over 6 months (data not shown). A slight drop in potency was observed for the freeze-thawed Buffer-14 formulation at the 6 month time point for all HPV types; similar to that observed after storage at −70° C. for over 6 months. Thus, the stability of the HPV antigens in various buffers that contain salt, excipients or combination of both was not impacted by the freeze-thaw process and long term storage.

The Biacore results of the lyophilized HPV formulations that were stored at 2-8° C. for over 6 months indicated that the antigenicity for all HPV types dropped for Buffer-B (Buffer-14) at all time points, including T=0, as compared to HPV formulations in Buffer-C and Buffer-D (data not shown). The results for the Buffer-14 composition, which lacks sucrose and mannitol, were similar to those obtained following storage at −70° C. as discussed above, and support the conclusion that the formulation could not sustain the freeze drying stress and the storage thereafter due to the lack of stabilizers. Unlike the results obtained with Buffer B, antigenicity for all HPV types in test formulations with Buffer-C and Buffer-D was identical to the reference standards. The data indicate that lyophilized test formulations in Buffer-C and Buffer-D were storage stable for longer than 6 months at 2-8° C., which demonstrates that the combination of excipients mannitol and sucrose in the buffers were able to maintain the integrity of the HPV VLPs. The results illustrate that the Buffer 14 containing formulation, which comprised salt but no mannitol or sucrose could not sustain the lyophilization stress.

Figure 11A:
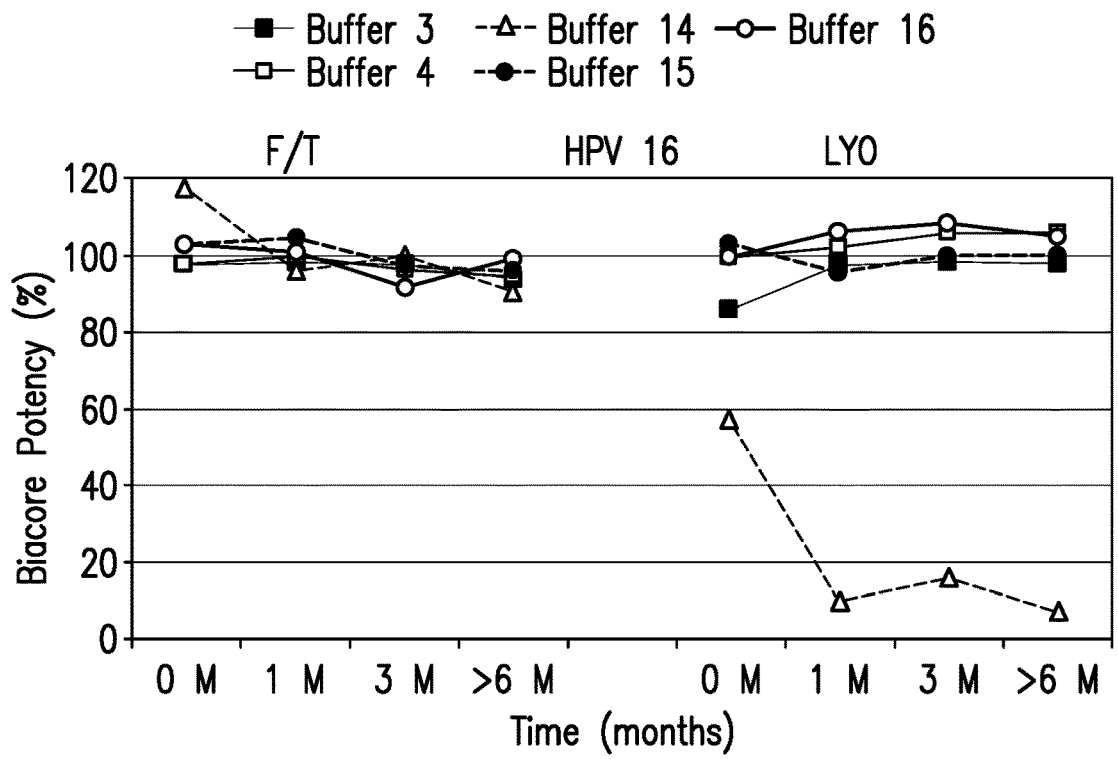
FIGS. 11A and 11B provide the in vitro antigenicity for HPV types 16 (FIG. 11A) and HPV18 (FIG. 11B) in the 4-valent test formulations (Buffer-B through Buffer-D), after storage for various time points at 25° C. Test formulations were stored after being subjected to freeze-thaw or lyophilization processes. See Example 6.
Figure 11B:
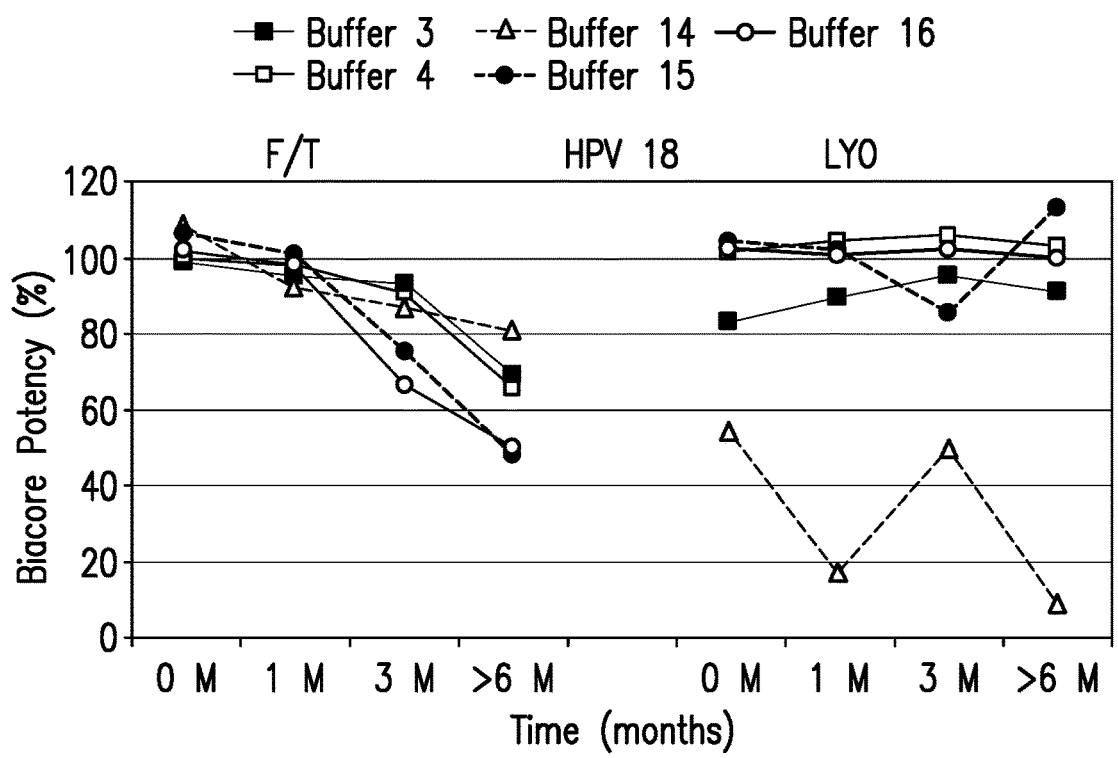
Figure 12A:
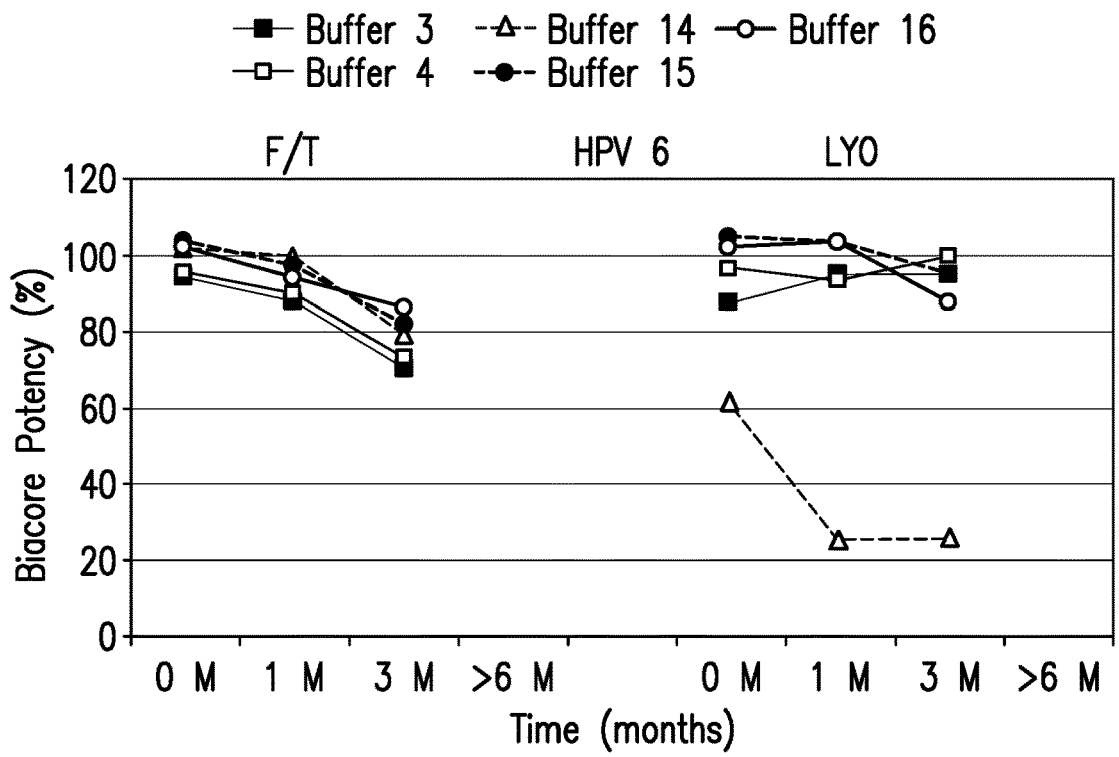
FIGS. 12A-12D provide the in vitro antigenicity for each of the HPV types in the 4-valent test formulations (Buffer-B through Buffer-D) following storage at 37° C. for various time points. Test formulations were stored after they were subjected to freeze-thaw or lyophilization processes. See Example 6. Plots are provided for HPV type 6 (FIG. 12A), HPV type 11 (FIG. 12B), HPV type 16 (FIG. 12C), and HPV type 18 (FIG. 12D).
Figure 12B:
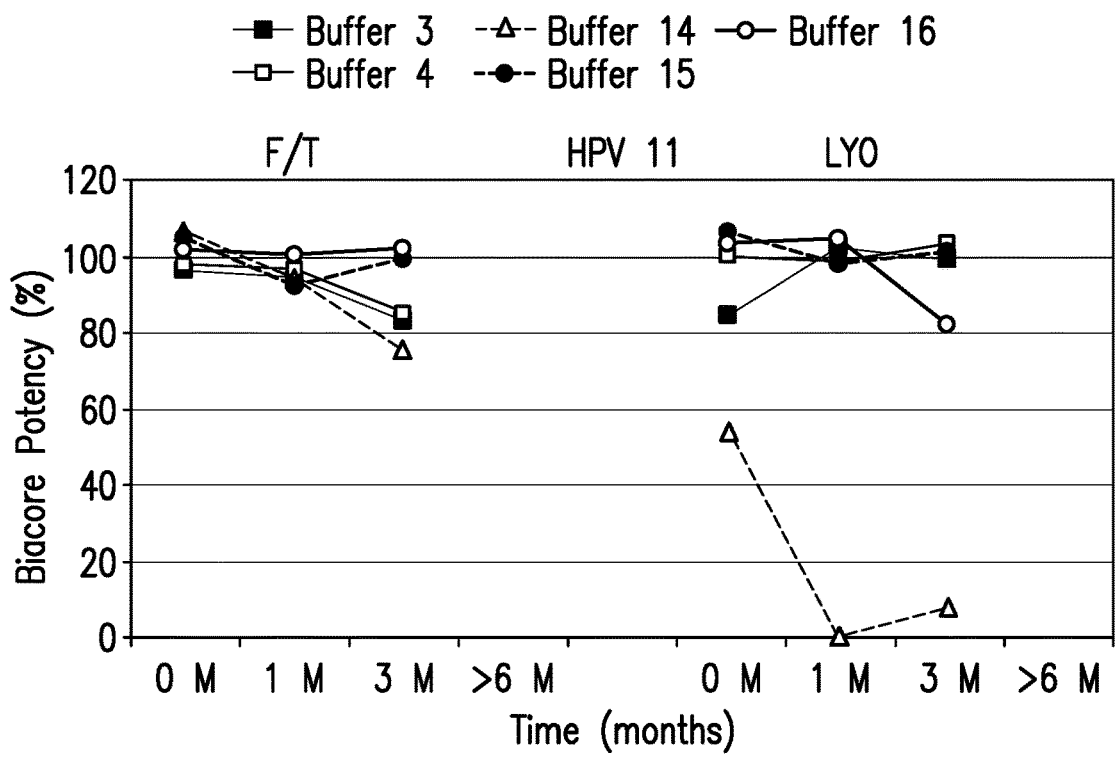
Figure 12C:
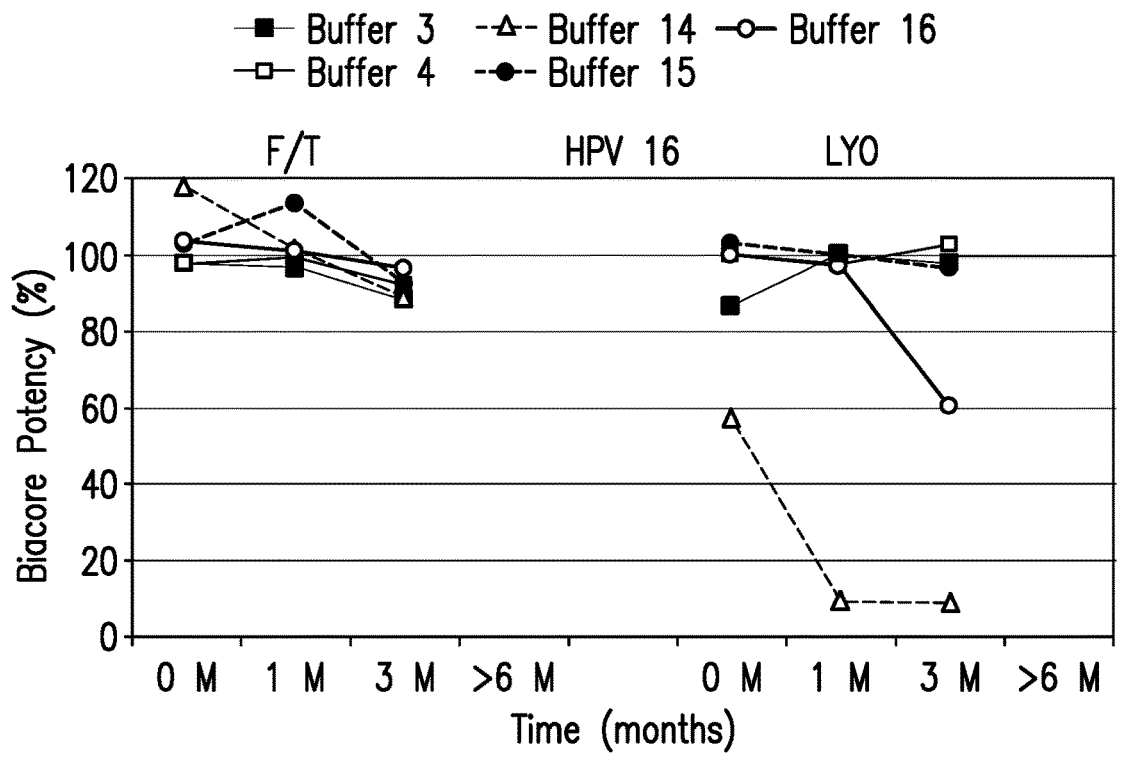
Figure 12D:
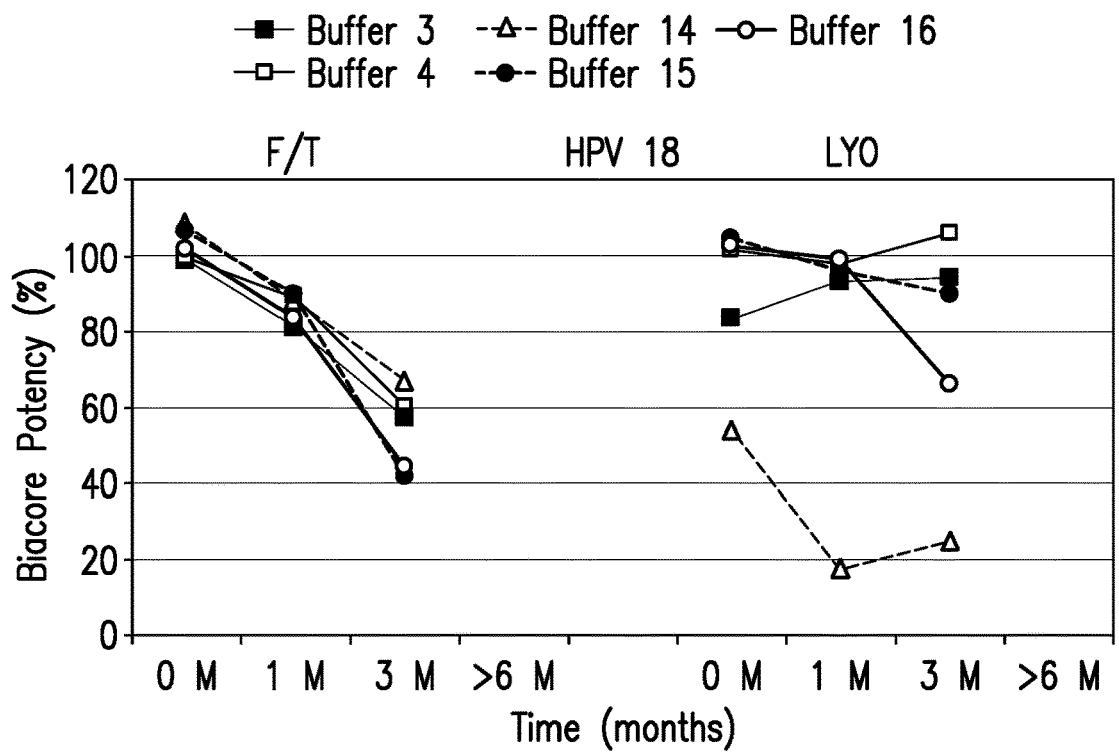

All 4-valent HPV vaccine formulations (Buffer-B through Buffer-D) that underwent the freeze-thaw process followed by storage at 25° C. for over 6 months were fully potent, and possessed almost identical Biacore responses as the reference standards for HPV types 6, 11 and 16 tested at various time points (representative results for types HPV16 and HPV18 are provided in FIG. 11). The antigenicity of HPV 18 dropped in formulations comprising Buffer-15 and Buffer-16 at the 3- and 6-month time points. A drop in antigenicity was also observed for HPV18 in formulations containing Buffer-3 and Buffer-4, but the drop was considerably less at the 6 month time point than that observed for formulations containing Buffer-15 and Buffer-16. Results indicate that under the conditions specified above, the presence of excipients in the freeze-thawed HPV type 18 formulations was not able to sustain the thermal stress for the specified length of time.

The Biacore results of the lyophilized HPV formulations that were stored at 25° C. for over 6 months indicated that the antigenicity for all the HPV types dropped for Buffer-B (Buffer-14) at all the time points including T=0 as compared to HPV formulations in Buffer-C and Buffer-D (representative results for HPV types 16 and 18 are provided in FIG. 11). The drop in antigenicity for Buffer-B was significant beyond the T=0 time point, which could be due to thermal instability following lyophilization of the HPV types at 25° C. For formulations comprising Buffer-C and Buffer-D, the antigenicity was retained and possessed almost identical Biacore response as the reference standards for all four HPV types tested at various time points. The storage stability observed for the lyophilized HPV formulations (Buffer-C and Buffer-D) beyond 6 months at 25° C. demonstrates that the combination of excipients, mannitol and sucrose in the formulation buffers was able to sustain the thermal as well as the lyophilization stress, thus maintaining the integrity of the HPV VLPs. Biacore results show that the loss of potency under the test conditions was directly influenced by the storage temperature, with greater loss of potency observed under higher storage temperature.

All 4-valent HPV vaccine formulations (Buffer-B through Buffer-D) that underwent the freeze-thaw process showed a drop in potency for all HPV types after 1 month of storage at 37° C. (FIG. 12). Thus, the results indicate that the presence of excipients in the freeze-thawed HPV formulations was not able to sustain the thermal stress after 1 month at 37° C. The Biacore results of the lyophilized HPV formulations that were stored at 37° C. for 3 months indicated that the antigenicity for all HPV types dropped for Buffer-B (Buffer-14) at all time points including T=0. At the 3 month time point, almost identical Biacore responses were observed for all HPV types in test formulations comprising Buffer-C (Buffer-3 and Buffer-15) and Buffer-D (Buffer-4) compared to the reference standards, indicating that antigenicity was retained. A drop in potency was observed, however, for HPV types in formulations comprising Buffer-16 at the 3 month time point. The storage stability of the lyophilized HPV formulations beyond 1 month at 37° C. supports the conclusion that that the combination of excipients mannitol and sucrose in the formulation buffers was able to sustain the thermal and lyophilization stress. Again, the loss of potency under the test conditions was influenced by storage temperature, with greater loss of potency observed under higher storage temperatures. In general, the reaction rate as defined by the VVM equivalence (Vaccine Vial Monitors) in the current experiment should fall into a VVM 30 category, which is a high stability indicator.

Example 7

Osmolality Measurements.

Osmolality of lyophilized HPV formulations and lyophilized 1×MAA formulations that were stored at 2-8° C. for 1 month was measured as described in Example 1. Results indicate that there was an increase in osmolality values for formulations comprising buffers containing salt (Buffer 14, Buffer 15 and Buffer 16) for both HPV and 1×MAA formulations (data not shown). The contribution to the osmolality is mainly from the excipients (mannitol and sucrose) and salt (sodium chloride) and not from the histidine, HPV antigens or 1×MAA adjuvant. The combination of salt and excipients play a major role in defining the tonicity of the given HPV 4-valent vaccine formulation.

Example 8

Particle Size Measurements

Static Light Scattering.

A static light scattering technique was used to measure particle size on all 1×MAA formulations that contained either 0 or 320 mM NaCl concentration (Buffer-A through Buffer F) as described in Example 1. Particle sizes for these 1×MAA formulations, which were either flash freeze-thawed (F/T FF 1×) or lyophilized (LYO FF), were compared to control formulations in the same buffers (Buffer-A through Buffer-F) that were not freeze-thawed or lyophilized.

The particle size of 1×MAA in control formulations (with and without salt) was around 4 to 9 μm, with the exception of Buffer-E (Buffer-5; 0 mM sodium chloride), which had a significant particle size of 25 μm (data not shown). Significant aggregation of 1×MAA, as illustrated by particle size increment, suggests the addition of salt (comparing Buffer-5 (0 mM sodium chloride) with Buffer-17 (320 mM salt)) in preventing MAA aggregation under both freeze-thaw and lyophilization conditions, respectively. Also, the ability of the excipient combination mannitol and sucrose (comparing Buffer-5 (sucrose only) with Buffer-4 and Buffer-3 (combination of sucrose and mannitol in the absence of salt)) to prevent MAA aggregation was observed. Under all test conditions, the least amount of aggregation in the absence of salt, was observed for formulations containing 6% mannitol and 4% sucrose. This observation was consistent with the long term storage stability trend observed for HPV antigens in the presence of sucrose and mannitol, which shows the ability of formulations comprising this combination to sustain freeze-thaw and lyophilization stress.

Dynamic Light Scattering.

Particle size was also measured using a dynamic light scattering technique on all the freeze-thawed and lyophilized 4-valent HPV vaccine formulations following storage at various temperatures for 1 month as described in Example 1. Particle size was also measured for control HPV vaccine formulations in the same buffers (Buffer-B through Buffer-D) that were not freeze-thawed or lyophilized. All samples were treated with the aluminum dissolution method described in Example 1 to release the HPV VLP antigens from the aluminum adjuvant prior to particle size measurements. The particle size distribution is the average measure of the size distribution of all the HPV VLPs present in the solution after aluminum dissolution.

Results indicate that the particle size distribution for the freeze-thawed HPV formulations stored at various temperatures for 1 month were comparable to control formulations that were neither freeze-thawed nor lyophilized, except for HPV formulation in Buffer-14 stored at 37° C. for 1 month (data not shown). Large particle size was observed for this formulation (Buffer-14) stored at 37° C. for 1 month, which could be due to thermal instability of the HPV VLPs after freeze-thaw stress. This data is consistent with the conclusion that this formulation could not sustain the freeze-thaw stress due to the lack of excipients other than salt. For the lyophilized HPV test formulations stored at various temperatures for 1 month, the particle size was comparable to the control formulations that were neither freeze-thawed nor lyophilized, except for the HPV formulation comprising Buffer-14 stored at 2-8° C. for 1 month. Large particle size was observed for this formulation indicating that this formulation was not able to sustain the lyophilization stress. Among the various HPV formulations evaluated, those with Buffer-C and Buffer-D, which comprise a combination of excipients (mannitol and sucrose), were impacted less by the stress of the freeze-thaw conditions as far as the particle size distribution of the VLPs compared to those formulations (Buffer-B) that did not comprise a combination of the excipients mannitol and sucrose.

Overall, the results indicate that the presence of this combination of excipients (mannitol and sucrose), with or without sodium chloride, was able to preserve the integrity of the HPV VLPs that were bound to the MAA during freeze-thaw and lyophilization process conditions.

Example 9

Characteristics of Lyophilized 4-Valent HPV Formulations & 1×MAA Formulations

Dry Cake Physical Appearance.

The physical appearance of all the lyophilized cakes was photographed after lyophilization (T=0) and at every time point during the course of the stability study at various temperatures. The appearance of the cakes was visualized by two analysts and based on the morphology, color, and other quality attributes, the cakes were categorized as described in Example 1. In general, dry white solid cakes were obtained for all 4-valent HPV formulations as well as for the 1×MAA formulations (see FIGS. 13 and 14). The physical appearance of each of the lyophilized HPV formulations was comparable to the physical appearance of the lyophilized 1×MAA formulations for all time points and storage temperatures. Elegant cakes were observed for formulations containing Buffer-3 and Buffer-4, and slightly collapsed or cracked or shrunk cakes for were observed for formulations containing Buffer-15 and Buffer-16. Completely collapsed cakes were observed for formulations containing Buffer-14 following lyophilization. No color change was observed for any of the formulations due to the thermal degradation of excipients. Results from this study indicate that the physical appearance of the cake was dependent on the formulation excipients and not on the storage temperature or the duration of storage. The quality of the cakes for formulations that contained a combination of the excipients of mannitol and sucrose decreased with increase in salt concentration.

Reconstitution Time.

The lyophilized 4-valent HPV vaccine formulations and 1×MAA formulations were reconstituted with sterile WFI based on the amount of excipients present. The volume of WFI that was added to each formulation ranged from 0.50 and 0.60 ml. The final volume after reconstitution was approximately 0.6 ml. The reconstitution time was monitored using a stop watch and the time for complete dissolution (in this case homogeneous suspension) was recorded for each of the lyophilized HPV vaccine formulations as well as the lyophilized 1×MAA formulations. The reconstitution time for all lyophilized HPV formulations were comparable to all the lyophilized 1×MAA formulations for all the time points and storage temperatures (data not shown). Almost all the formulations had a fast reconstitution time of less than 60 seconds irrespective of the storage temperature and duration of storage.

Shake Test.

After reconstitution of all the lyophilized 4-valent HPV vaccine formulations and 1×MAA formulations, a shake test was performed to check the quality of the vaccine/adjuvant formulation. The time for the alum particles to settle at the bottom of the vial was measured for each of the test formulations that were either freeze-thawed or lyophilized. Results indicate that all 4-valent HPV formulations that contained salt (Buffer-14, Buffer-15 and Buffer-16) had a faster settling time than formulations without salt, indicating that the alum particles were agglomerated (see FIG. 15). For 4-valent HPV formulations that contained mannitol and sucrose in the absence of salt (Buffer-3 and Buffer-4), the settling time was greater than 15 minutes, indicating that the alum particles were not agglomerated. Thus, the presence of excipients in the 4-valent HPV vaccine formulation prevents the agglomeration of alum particles even after freeze thaw and lyophilization stress. The storage time and temperature did not have any significant impact on the shake test results.

Shake test results for the 1×MAA formulations indicate that the freeze-thaw stress did not impact the settling time at any given time point or storage temperature, as all test formulations that contained excipients and salt had a settling time of greater than 15 min, while the formulation that contained only salt (Buffer-14), had a slightly faster settling time though not significantly different from the rest of the formulations (data not shown). For lyophilized 1×MAA formulations that contained mannitol and sucrose in the absence of salt (Buffer-3 and Buffer-4), the settling time was greater than 15 minutes, indicating that the alum particles were not agglomerated. Thus, the presence of excipients in the 1×MAA formulations prevented the agglomeration of alum particles after lyophilization stress. The storage time and temperature did not have any significant impact on the shake test results.

What is claimed is:

1. A lyophilized human papillomavirus vaccine (HPV) formulation comprising:
a) a therapeutically effective amount of HPV virus-like particles (VLPs) of at least one HPV type which are adsorbed onto an aluminum adjuvant wherein the VLPs of each HPV type are present in a concentration of 10-200 mcg/ml and wherein the VLPs are selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; and;
b) 4% to 7% w/v mannitol and 1% to 5% w/v sucrose; and
c) optionally a salt,
wherein the formulation is stable for a time period of 6 months at 25° C. and for a time period of 3 months at 37° C. following lyophilization, wherein the formulation is stable if the HPV VLPs retain potency over the time period at the indicated temperature, as measured in a Biacore assay.

2. The formulation of claim 1, further comprising about 0.15 M to about 0.32M NaCl.

3. The formulation of claim 2, further comprising about 5 mM to about 20 mM histidine.

4. The formulation of claim 3, further comprising about 0.01% to about 0.03% weight to volume concentration of a surfactant selected from the group consisting of Polysorbate 20 and Polysorbate 80.

5. The formulation of claim 4, wherein the surfactant is Polysorbate 80 which is present in a weight to volume concentration of about 0.01%.

6. The formulation of claim 1, wherein the aluminum adjuvant is selected from the group consisting of aluminum hydroxide, aluminum phosphate, and aluminum hydroxyphosphate.

7. The formulation of claim 6, wherein the HPV VLPs are from HPV types 6, 11, 16 and 18.

8. The formulation of claim 7, further comprising HPV VLPs of at least one additional HPV type selected from the group consisting of: 31, 33, 45, 52 and 58.

9. A lyophilized human papillomavirus vaccine (HPV) formulation comprising:
a) a therapeutically effective amount of HPV virus-like particles (VLPs) of at least four HPV types which are adsorbed onto an aluminum adjuvant, wherein the VLPs of each HPV type are present in a concentration of 10-200 mcg/ml and wherein the VLPs are selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; and;
b) 4% to 7% w/v mannitol and 1% to 5% w/v sucrose; and
c) optionally a salt,
wherein the formulation is stable for a time period of 6 months at 25° C. and for a time period of 3 months at 37° C. following lyophilization, wherein the formulation is stable if the HPV VLPs retain potency over the time period at the indicated temperature, as measured in a Biacore assay.

10. A lyophilized human papillomavirus vaccine (HPV) formulation comprising:

a) a therapeutically effective amount of HPV virus-like particles (VLPs) of at least six HPV types which are adsorbed onto an aluminum adjuvant, wherein the VLPs of each HPV type are present in a concentration of 10-200 mcg/ml and wherein the VlPs are selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; and;
b) 4% to 7% w/v mannitol and 1% to 5% w/v sucrose; and
c) optionally a salt, wherein the formulation is stable for a time period of 6 months at 25° C and for a time period of 3 months at 37° C. following lyophilization, wherein the formulation is stable if the HPV VLPs retain potency over the time period at the indicated temperature, as measured in a Biacore assay.

11. A lyophilized human papillomavirus vaccine (HPV) formulation comprising:

a) a therapeutically effective amount of HPV virus-like particles (VlPs) of at least nine. HPV types which are adsorbed onto an aluminum adjuvant, wherein the VLPs of each HPV type are present in a concentration of 10-200 mcg/ml and wherein the VLPs are selected from the group consisting of: HPV6, HPV11, HPV16, HPV18, HPV26, HPV31, HPV33, HPV35, HPV39, HPV45, HPV51, HPV52, HPV53, HPV55, HPV56, HPV58, HPV59, HPV66, HPV68, HPV73, and HPV82; and;
b) 4% to 7% w/v mannitol and 1% to 5% w/v sucrose; and
c) optionally a salt, wherein the formulation is stable for a time period of 6 months at 25° C. and for a time period of 3 months at 37° C following lyophilization, wherein the formulation is stable if the HPC VLPs retain potency over the time period at the indicated temperature, as measured in a Biacore assay.

* * * * *